United States Patent [19]
Takada et al.

[11] Patent Number: 5,481,107
[45] Date of Patent: Jan. 2, 1996

[54] MASS SPECTROMETER

[75] Inventors: Yasuaki Takada, Kokubunji; Minoru Sakairi, Kawagoe; Atsumu Hirabayashi, Kokubunji; Youichi Ose, Mito, all of Japan

[73] Assignee: Hitachi, Ltd., Tokyo, Japan

[21] Appl. No.: 302,555

[22] Filed: Sep. 8, 1994

[30] Foreign Application Priority Data

Sep. 20, 1993 [JP] Japan .................. 5-232833

[51] Int. Cl.[6] ........................... H01J 49/06
[52] U.S. Cl. ......................... 250/281; 250/288
[58] Field of Search ................... 250/281, 288, 250/288 A

[56] References Cited

U.S. PATENT DOCUMENTS 4,999,492  3/1991  Nakagawa ................. 250/288

FOREIGN PATENT DOCUMENTS 0237259  9/1987  European Pat. Off. ........ 250/281
278143   3/1990  Japan .

OTHER PUBLICATIONS

Analytical Chemistry, vol. 59, No. 22, Nov. 15, 1987, pp. 2642–2646 (see Specification pp. 2 and 3).

Primary Examiner—Jack I. Berman
Attorney, Agent, or Firm—Kenyon & Kenyon

[57] ABSTRACT

A mass spectrometer comprising an ionization region for ionizing a sample under atmospheric pressure, an ion sampling aperture for introducing ions generated by the ionization region into a vacuum, and a mass analysis region for mass analyzing the ions on the basis of a high-frequency electric field, wherein: an electrostatic lens for deflecting the direction of the movement of the ion from the center axis of the ion sampling aperture is disposed between the ionization region and the mass analysis region; the center axis of an aperture for introducing ions into the mass analysis region and the center axis of the ion sampling aperture are disposed so as to be shifted in parallel from each other; and the center axis of the ion sampling aperture and the center axis of a cylindrical inner electrode constituting the electrostatic lens are disposed so as to be shifted in parallel from each other to thereby prevent charged droplets or droplets without charge from flowing into the mass analysis region.

43 Claims, 16 Drawing Sheets

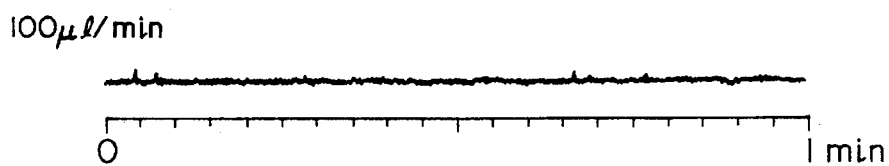
FIG. 21A
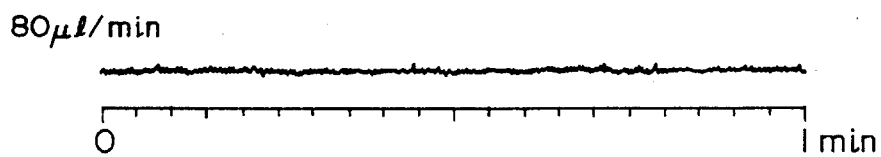
FIG. 21B
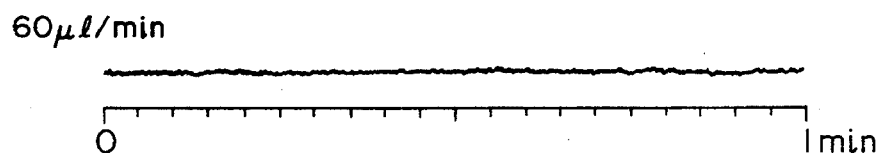
FIG. 21C
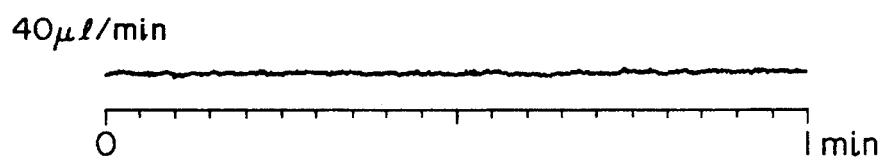
FIG. 21D
FIG. 22
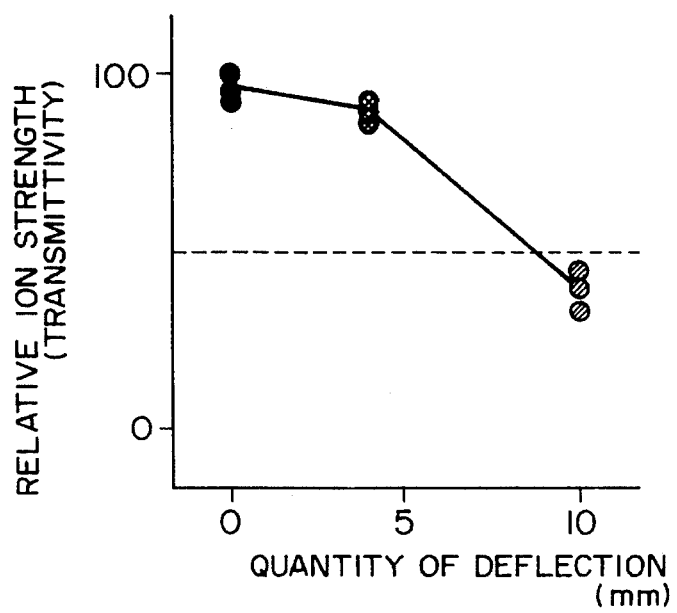

MASS SPECTROMETER

BACKGROUND OF THE INVENTION

The present invention relates to an apparatus constructed by a combination of a mixture separating means and a mass spectrometer, which apparatus is important for separation and analysis of human body relating mixture compounds such as saccharides, peptides, proteins, and so on. Particularly, it relates to a liquid chromatograph/mass spectrometer and a capillary electrophoresis/mass spectrometer.

At present, importance is attached to the development of a method for mass analysis of human body relating compounds in the field of analysis. Human body relating compounds are generally existing as mixture compounds in solution. The development of an apparatus constructed by a combination of a mixture separating means and a mass spectrometer has progressed. A liquid chromatograph/mass spectrometer is a typical example of the apparatus. A liquid chromatograph is superior in separation of mixture compounds but it cannot identify compounds. On the other hand, a mass spectrometer is superior in the ability of identifying compounds sensitively but it cannot analyze mixture compounds. Therefore, a liquid chromatograph/mass spectrometer using a mass spectrometer as a detector of a liquid chromatograph is very effective for analysis of mixture compounds.

FIG. 23 is a block diagram showing the overall structure of a conventional liquid chromatograph/mass spectrometer. A sample solution separated by a liquid chromatograph 1 is introduced through a connecting tube 2 into an ion source 3. The ion source 3 is controlled by an ion source power supply 4 through a signal line 5a. Ions concerning sample molecules, which are generated by the ion source 3, are introduced to a mass analysis region 6 and mass analyzed. The mass analysis region 6 is evacuated to a vacuum by a vacuum system 7. The ions thus mass analyzed are detected by an ion detector 8. A detection signal is fed through a signal line 5b to a data processing unit 9.

As described above, the principle of the liquid chromatograph/mass spectrometer is simple but there arises a problem that the liquid chromatograph using samples in solution is incompatible with the mass spectrometer using ions in a vacuum. Accordingly, the development of an apparatus constructed by a combination of a liquid chromatograph and a mass spectrometer and the development of a method therefor are attended with great difficulties. There have been developed some methods to solve this problem. Of the methods, the likeliest is a spray ionization method in which an effluent from a liquid chromatograph is nebulized so that sample molecules contained in generated droplets are ionized and introduced into a mass analysis region.

As an example of the spray ionization method, an electrospray method described in Analytical Chemistry, 59, 2642 (1987) will be described below. FIG. 24 is a sectional view showing the structure of a liquid chromatograph/mass spectrometer equipped with an electrospray ion source. A sample solution eluted from a liquid chromatograph 1 is introduced through a connecting tube 2 and a connector 10 into a capillary 11 for nebulization. By application of a voltage of the order of kV between the nebulization capillary 11 and a counter electrode 12, small charged droplets of the sample solution are conically nebulized from an end of the nebulization capillary, that is, a so-called electrospray phenomenon occurs. In the electrospray method, an output 13 for nebulizing gas is provided so that gas such as nitrogen gas is poured from the surroundings of the nebulization capillary 11 to thereby accelerate the vaporization of the small charged droplets. Further, the gas such as nitrogen gas is blown toward the generated small charged droplets from an outlet 14 for vaporizing gas provided in the counter electrode 12 side to thereby accelerate the vaporization of the small charged droplets. Ions thus generated are introduced through an ion sampling aperture 15 into a vacuum 6 and mass analyzed by a mass analysis region 6 under a high vacuum.

On the other hand, a structure shown in FIG. 25 was conventionally used as an ion detector to improve the signal-to-noise ratio (SIN) in the mass spectrometer. An ion deflecting electrode 16 is provided in the rear portion of a mass analysis region 6 for mass separation under a high-frequency electric field to deflect mass-separated ions. The deflected ions are accelerated at a voltage of the order of kV and collide with a dynode 17 to produce secondary electrons. Secondary electrons are emitted from the secondary electron-producing dynode 17 with which the ions collide. The emitted secondary electrons are detected by an electron detector 18 such as an electron multiplier. By the structure shown in FIG. 25, neutral molecules having no charge, charged droplets or droplets having no charge are prevented from being detected as a signal by the ion detector 8, so that improvement in S/N is attained to some degree.

SUMMARY OF THE INVENTION

The aforementioned conventional methods have the following problems. The ion sampling aperture for passing ions is not only pervious to ions but also pervious to charged droplets insufficient in vaporization or droplets having no charge (hereinafter referred to as "droplets without charge" in this specification). Such charged droplets or droplets without charge are large in size, so that it is impossible to remove such droplets thoroughly in the mass analysis region for mass separation under a high-frequency electric field. The charged droplets or the droplets without charge contaminate the mass analysis region thereby preventing the long-term stable operation of the mass analysis region, and/or introducing additional noise to the ion detector. This additional source of noise reduces the S/N and thus, the sensitivity of the mass spectrometer. In the prior art structure shown in FIG. 25 to improve the S/N of the mass spectrometer, a great part of charged droplets or droplets without charge are drawn out to a secondary electron-producing dynode 17 to reduce the noise. Further, the reduction of contamination of a mass analysis region 6 is a problem to be solved. If efficiency in vaporization of charged droplets or droplets without charge in the ion source is improved so that the charged droplets or droplets without charge can be eliminated thoroughly, the charged droplets or droplets without charge as a noise source are removed. If energy such as heat energy sufficient to vaporize charged droplets or droplets without charge is applied to the charged droplets or droplets without charge, human body relating compounds which are apt to be dissociated, however, may be decomposed. Therefore, the development of an apparatus/method for separating ions from charged droplets or droplets without charge so as to introduce the ions into the mass analysis region selectively has been required.

An object of the present invention is to provide a noiseless high-sensitive mass spectrometer in which stable analysis can be made for a long term.

In the present invention, ions are separated from charged droplets or droplets without charge and selectively introduced into a mass spectrometer. In an ionization portion, the separated sample is ionized under atmospheric pressure. The generated ions are introduced through an ion sampling aperture into a vacuum and the introduced ions are mass analyzed on the basis of a high-frequency electric field. The center axis of an aperture for introducing ions into a mass analysis region and the center axis of the ion sampling aperture are arranged in parallel and offset from each other to thereby prevent the charged droplets or droplets without charge from flowing into the mass analysis region. The two center axes are arranged so that the projection of the ion introducing aperture onto a plane perpendicular to the two center axes and the projection of the ion sampling aperture onto the plane do not overlap each other.

More specifically, an electrostatic lens for deflecting the generated ions from the center axis of the ion sampling aperture is provided so that the orbit of the ions and the orbit of the charged droplets or droplets without charge are separated from each other to thereby introduce the ions into the mass analysis region selectively. For example, the electrostatic lens is constituted by a cylindrical inner electrode and an outer electrode arranged in the outside of the inner electrode. A plurality of holes are formed at least in the inner electrode of the electrostatic lens.

In the aforementioned structure, ions can be introduced into the mass analysis region efficiently, so that both contamination of the mass analysis region with the charged droplets or droplets without charge and noise caused by the charged droplets or droplets with charge can be reduced. A high-sensitive mass spectrometer can be realized by the reduction of noise.

BRIEF DESCRIPTION OF THE DRAWINGS

FIGS. 20A–20D and FIGS. 21A–21D are views showing examples of measurement of noise levels obtained by the mass spectrometer in embodiments of the present invention.

FIG. 22 is a view showing relative signal strength obtained by the mass spectrometer in an embodiment of the present invention.

DETAILED DESCRIPTION

Referring to FIGS. 1 through 22, embodiments of the present invention will be described.

(First Embodiment)

Figure 1:
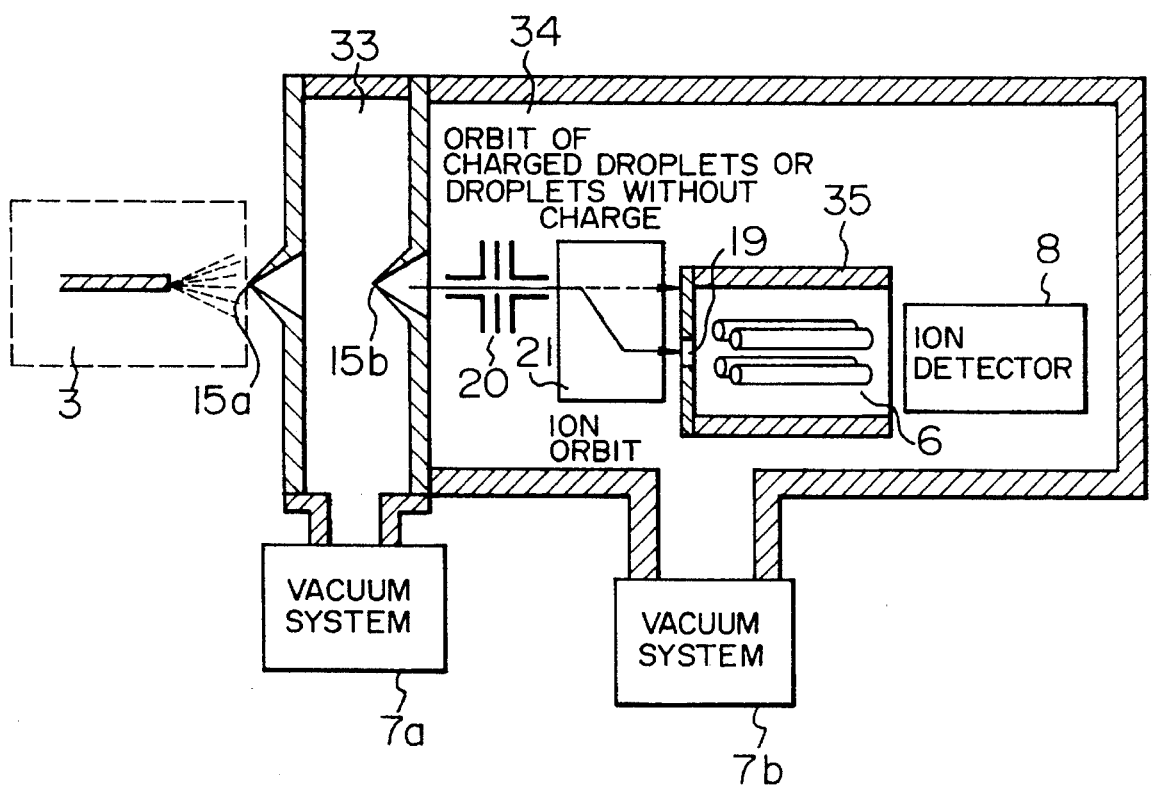
FIG. 1 is a view showing the structure of a mass spectrometer using an electrostatic lens for deflecting ions according to a first embodiment of the present invention.

FIG. 1 shows the structure of a mass spectrometer according to a first embodiment of the present invention. A sample solution separated by a sample separating means for separating a mixture in solution in a liquid chromatograph or the like is introduced into an ion source 3. Ions concerning sample molecules, generated by the ion source 3, are introduced into a vacuum region 34 through an ion sampling aperture 15a, an intermediate pressure region 33 evacuated by a vacuum system 7a and an ion sampling aperture 15b. When the ions are introduced into a vacuum, the ions are cooled by adiabatic expansion so that water molecules are attached to the ions, that is, so-called "clustering" occurs. To prevent the clustering, an electrode having the ion sampling apertures 15a and 15b is heated to about 100° C. by a heater.

In a mass analysis region 6, an aperture 19 for introducing ions is arranged in a position shifted from the center axis of the ion sampling apertures 15a and 15b. That is, the center axis of the ion introducing aperture 19 and the center axis of the ion sampling apertures 15a and 15b are arranged in parallel and offset with each other so that the projection of the ion introducing aperture 19 onto a plane perpendicular to these center axes does not overlap the projection of the ion sampling apertures 15a and 15b onto the plane.

Ions introduced into a vacuum are accelerated by an extracting electrode 20 composed of a single electrode or a plurality of electrodes, focused by an electrostatic lens 21 and then introduced into the quadrupole mass analysis region 6. The quadrupole mass analysis region is generally put into a metal cylinder 35 to avoid the influence of the outside field. The metal cylinder 35 is located in the vacuum region 34 evacuated by a vacuum system 7b. The deflecting of the direction of ions is performed by the electrostatic lens 21, so that ions separated from charged droplets or droplets without charge are introduced into the mass analysis region 6.

In the electrostatic lens 21 in FIG. 1, the solid line represents the orbit of ions and the broken line represents the orbit of charged droplets or droplets without charge. Ions, mass separated by the mass analysis region 6 under a high-frequency electric field, are detected by an ion detector 8. Because in the structure shown in FIG. 1, ions and charged droplets or droplets without charge are separated in a space between the ion sampling aperture 15b and the mass analysis region 6, the charged droplets or droplets without charge can be prevented from flowing into the mass analysis region 6, so that both contamination of the mass analysis region 6 and noise detected by the ion detector 8 can be reduced.

The principle of separation of charged droplets or droplets without charge from ions will be described below. When introduced into a vacuum from the ion sampling aperture 15b, ions and charged droplets are accelerated. Charged droplets larger in mass than ions are hardly deflected by the electric field of the electrostatic lens 21 because of kinetic energy obtained at this time, so that the charged droplets move on an orbit along the center axis of the ion sampling apertures 15a and 15b. On the other hand, kinetic energy given to ions lighter in weight than charged droplets at the time of inflow from the ion sampling aperture 15b is negligible compared with acceleration energy given by the electric field of the extracting electrode 20. Accordingly, the orbit of ions can be bent easily by the electric field of the electrostatic lens 21. In this manner, the orbit of light ions is separated from the orbit of heavy charged droplets on the basis of difference in kinetic energy at the time of introduction from the ion sampling aperture, so that ions can be introduced into the mass analysis region 6 selectively. It is also a matter of course that droplets without charge are separated from ions.

Figure 2:
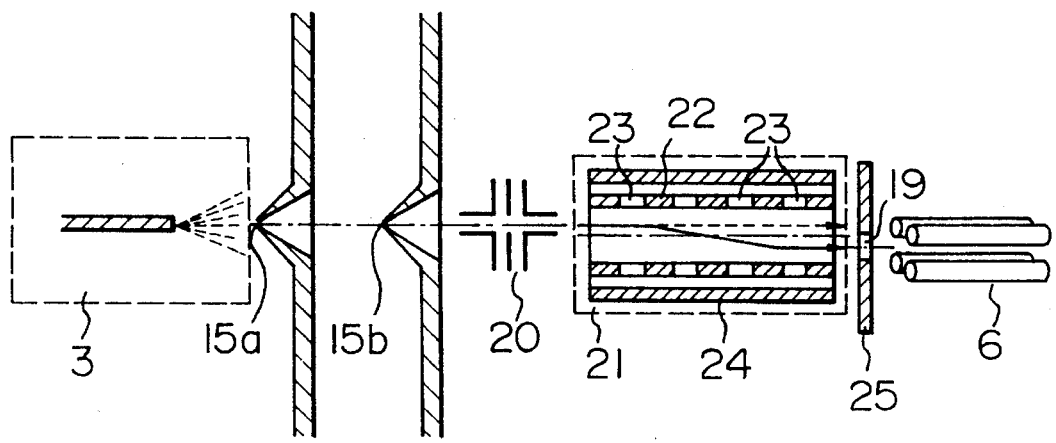
FIGS. 2, 3, 4 and 5 are sectional views showing examples of the electrostatic lens used in respective embodiments of the present invention.

Various structures may be considered to realize the electrostatic lens 21 for deflecting ions as shown in FIG. 1. For example, FIG. 2 shows a structure for deflecting ions by using an electrostatic lens composed of multiple concentrically-assembled cylindrical electrodes as described in JP-A-2-78143. An inner electrode 22 is equipped with a plurality of holes 23 through which the electric field of an outer electrode 24 penetrates into the inside of the inner electrode 22. A potential distribution for focusing ions is formed by the penetrated electric field. When the center axis of the concentrically cylindrical electrostatic lens 21 is offset from the center axis of the ion sampling apertures 15a and 15b, ions are deflected so as to move on the orbit represented by the solid line in the electrostatic lens 21 in FIG. 2. The mass analysis region 6 is arranged to align the ion introducing aperture 19 opening with the ion orbit at an end of the electrostatic lens 21. Charged droplets or droplets without charge move on an orbit represented by the broken line. Because charged droplets or droplets without charge collide with portions of electrode 25 other than the open ion introducing aperture 19 entrance into the mass analysis region 6 is prevented. The ions moved on the orbit of the solid line by deflection are introduced through the ion introducing aperture 19 into the mass analysis region. The electrode 25 is preferably heated by a heater or the like at this time to reduce the contamination of the electrode 25 having the ion introducing aperture 19 opened therein, due to the charged droplets or droplets without charge.

The feature of the electrostatic lens shown in FIG. 2 is that deflection of ions and focusing thereof can be achieved simultaneously by a single electrostatic lens constructed by two cylindrical electrodes. In the case where an electrostatic lens portion is to be formed generally, the respective electrodes constituting the electrostatic lens require processing accuracy. Where the respective electrodes are placed in predetermined positions, close attention is paid to assembling accuracy. This is because small difference in the arrangement of the respective electrodes greatly changes the ion orbit. To deflect and focus ions, a complicated potential distribution must be formed in the electrostatic lens portion. Accordingly, a large number of electrodes and a complicated structure are required, so that assembling efficiency deteriorates. Therefore, the number of electrodes constituting the electrostatic lens is preferably as small as possible. When an electrostatic lens constituted by two concentrically assembled cylindrical electrodes as shown in FIG. 2 is used and arranged so that the center axis of the electrostatic lens is shifted from the center axis of the ion sampling apertures, an apparatus with a favorable assembling efficiency and a simple structure can be produced because the number of electrodes constituting the electrostatic lens is only two.

An example of the size of the electrostatic lens shown in FIG. 2 will be described below. Assuming now that the inner diameter of the inner electrode 22, the inner diameter of the outer electrode 24, the axial length of the electrode and the difference between the center axis of the ion sampling apertures 15a and 15b and the center axis of the ion introducing aperture 19 are 20 mm, 30 mm, 15 cm and 4 mm respectively, then the S/N is increased by about eight times so that the sensitivity in the mass spectrometer is improved to be nearly about one order of magnitude. The inner diameter of the inner electrode is preferably in a range from 3 mm to 10 cm. The axial length of the electrode is preferably larger than the inner diameter of the inner electrode.

Figure 3:
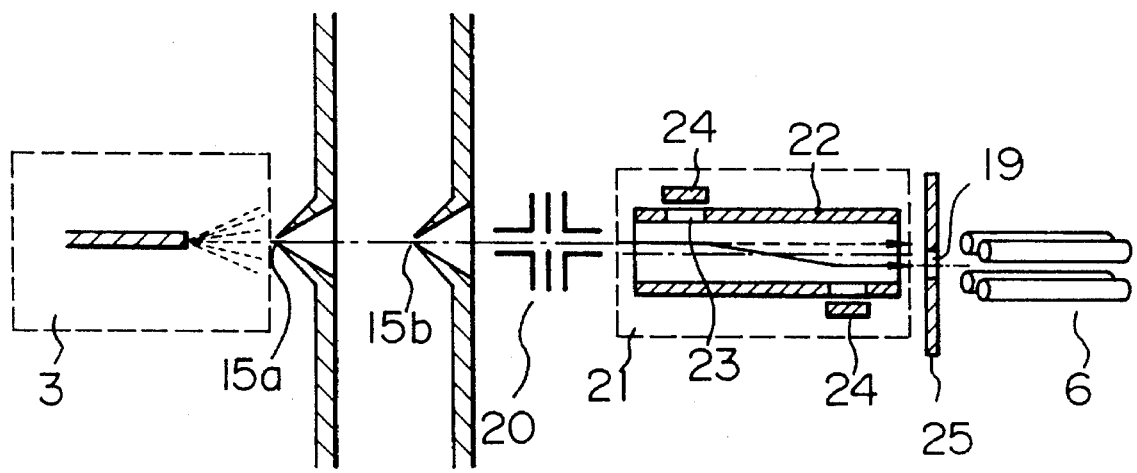
Figure 4:
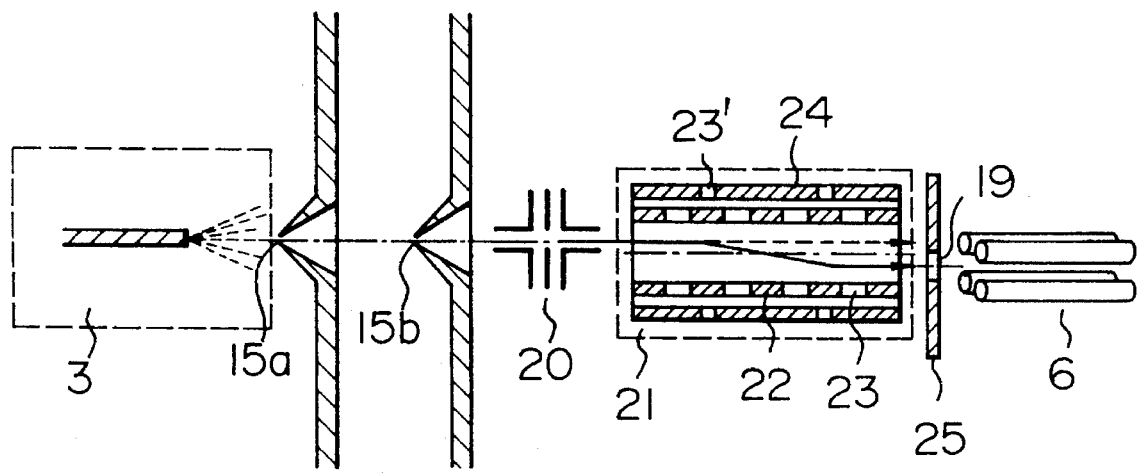
Figure 5:
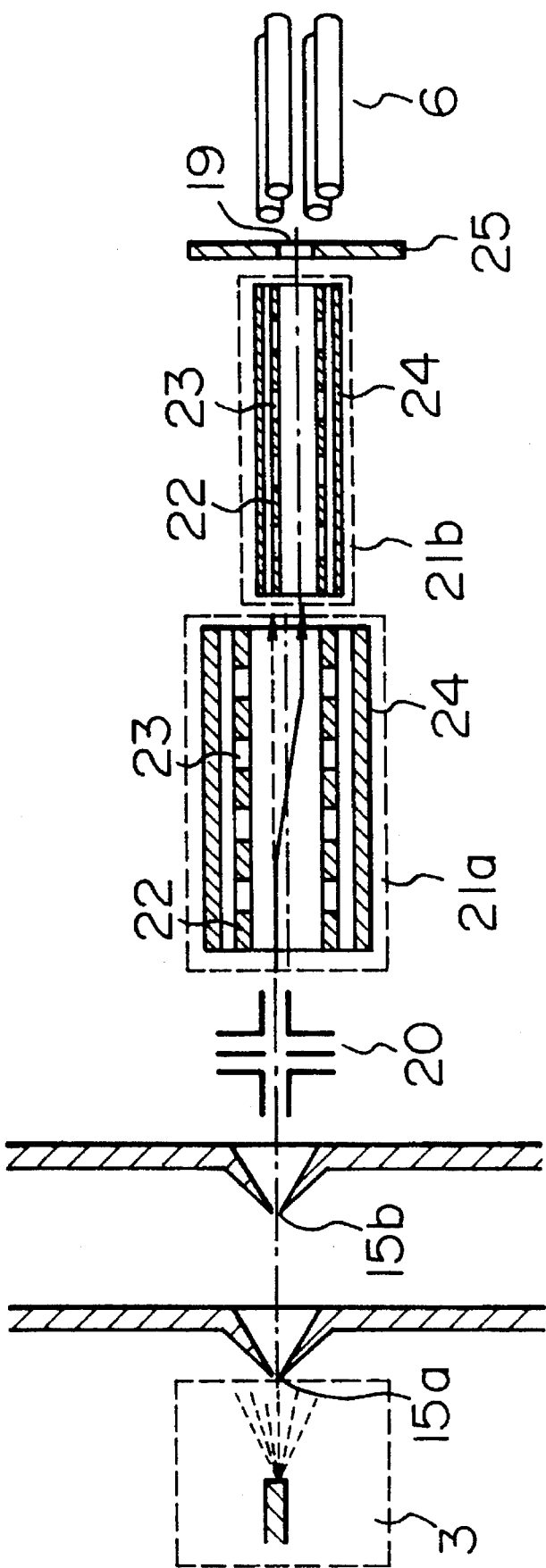

To form the ion deflecting and focusing electrostatic lens simply and accurately, the electrostatic lens is preferably constituted by inner and outer cylindrical electrodes arranged concentrically as shown in FIG. 2. The outer electrode 24 may be not always constituted by a single electrode. As shown in FIG. 3, plate-like individual outer electrodes 24 may be arranged outside opposite the holes 23 of the cylindrical inner electrode 22. In the case where evacuation conductance in the electrostatic lens portion is increased to thereby improve the degree of vacuum in the cylinder more greatly, evacuation holes 23' may be provided in the cylindrical outer electrode 24 as shown in FIG. 4. To further increase the evacuating efficiency, the outer electrode 24 may be constituted by metal meshes. In the case where ion energy is dispersed so that the dispersion of energy forms aberration to thereby spoil the focusing effect of the electrostatic lens portion, a plurality of electrostatic lenses 21a and 21b as shown in FIG. 5 may be arranged so that the electrostatic lens 21b having a smaller diameter than the inner diameter of the electrostatic lens 21a is placed in the rear portion of the first-stage electrostatic lens 21a to thereby increase the ion condensing effect. In this case, the center axis of the electrostatic lens 21b, placed nearer to the mass analysis region 6, is made to coincide with the center axis of the ion introducing aperture 19. The respective center axes of the electrostatic lenses 21a and 21b are arranged in parallel and offset from each other. Further, in FIGS. 1 through 5, the center axis of the ion introducing aperture 19 and the center axis of the mass analysis region 6 are coincident with each other and are arranged in parallel and offset from the center axis of the ion sampling apertures.

(Second Embodiment)

Figure 6:
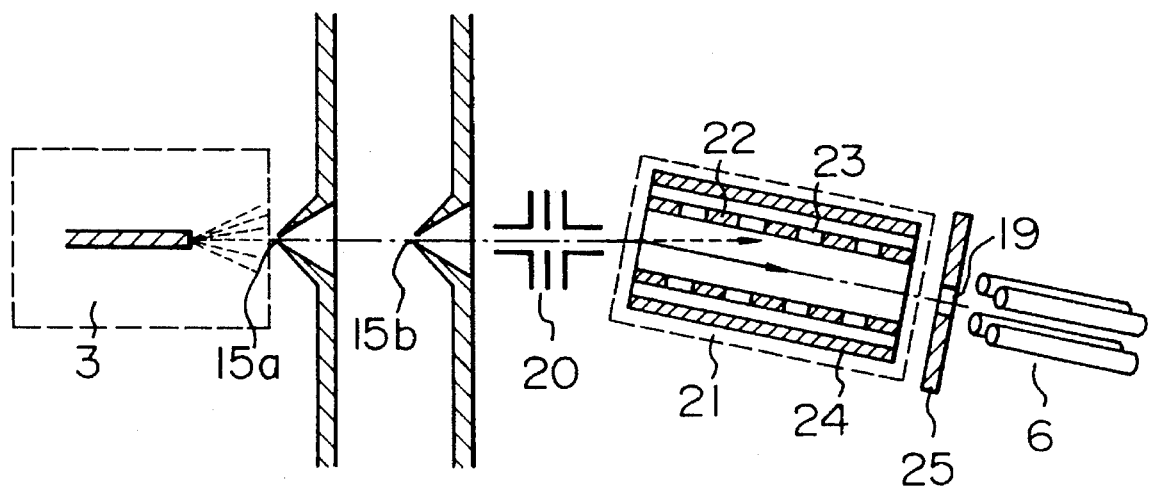
FIGS. 6 and 7 are views showing the structure of a mass spectrometer using an electrostatic lens for deflecting ions according to a second embodiment of the present invention.

FIG. 6 is a view showing a second embodiment of the present invention. When the center axis of the ion sampling apertures 15a and 15b and the center axis of the cylindrical electrostatic lens 21 are angled to cross each other so that the center axis of the ion sampling apertures passes through the center of the inlet of the electrostatic lens, the ion orbit is deflected in the direction of the center axis of the electrostatic lens 21 represented by the solid line in the electrostatic lens 21 and reaches the mass analysis region 6. Charged droplets or droplets without charge which are hardly deflected, however, move straight as represented by the broken line in the electrostatic lens 21 and collide with the inner wall surface of the electrostatic lens 21. Accordingly, charged droplets or droplets without charge are prevented from entering into the mass analysis region 6.

Figure 7:
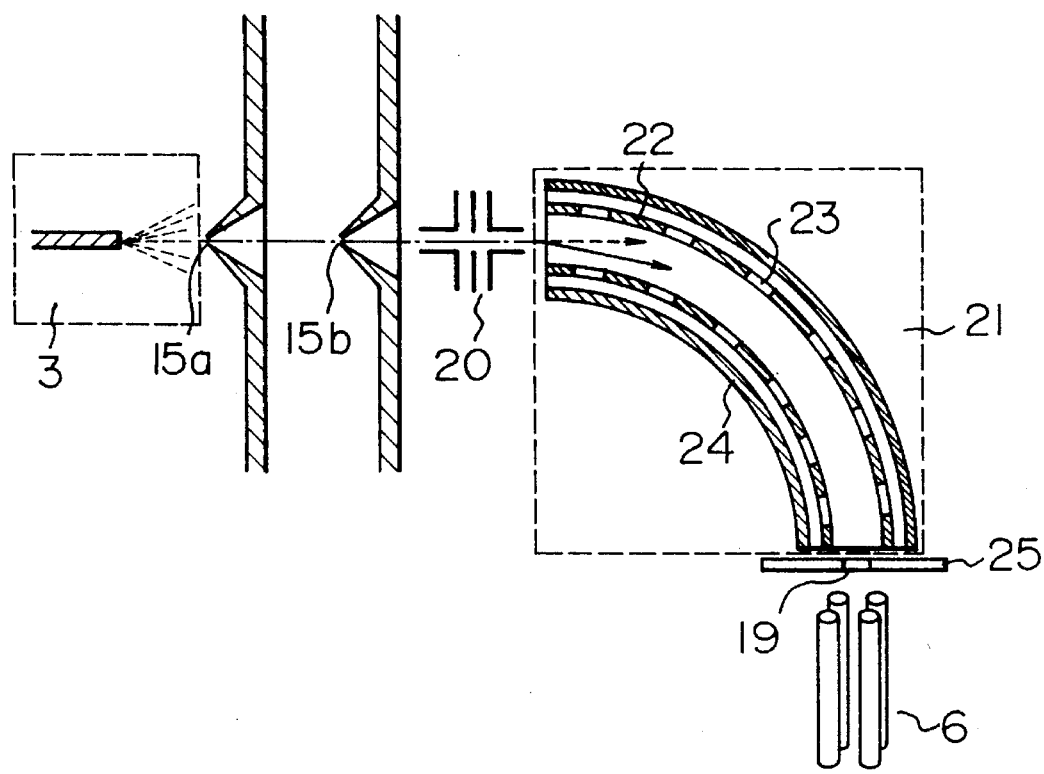

As shown in FIG. 7, curvature may be given to the center axis of the cylindrical electrodes constituting the electrostatic lens 21. The electrostatic lens is constituted by the inner and outer electrodes circularly shaped in section and has the shape of a part of a donut as the whole. Like the structure shown in FIG. 6, the center axis of the ion sampling apertures is arranged to pass through the center of the inlet of the electrostatic lens. Like the structure shown in FIG. 6, charged droplets or droplets without charge move straight and collide with the electrode, so that only the ions reach the mass analysis region 6. In the embodiment shown in FIGS. 6 and 7, the center axis of the ion introducing aperture 19 and the center axis of the mass analysis region 6 are coincident with each other and cross the center axis of the ion sampling apertures.

(Third Embodiment)

The structure of an electrostatic lens used in this embodiment of the present invention will be described below.

To easily form electrodes constituting an electrostatic lens, an electrically conductive thin-film pattern is formed in the inner or outer wall surface of an insulating tube. Alternatively, electrically conductive thin-film patterns may be formed in the inner and outer wall surfaces of the insulating tube so that the electrically conductive thin films formed on the inner and outer wall surfaces are used as inner and outer electrodes, respectively. The electrostatic lens 21 having the complicated structure as shown in FIG. 7 is formed by using an electrically conductive resin with favorable electrical conductivity that is easy to deform.

Figure 8:
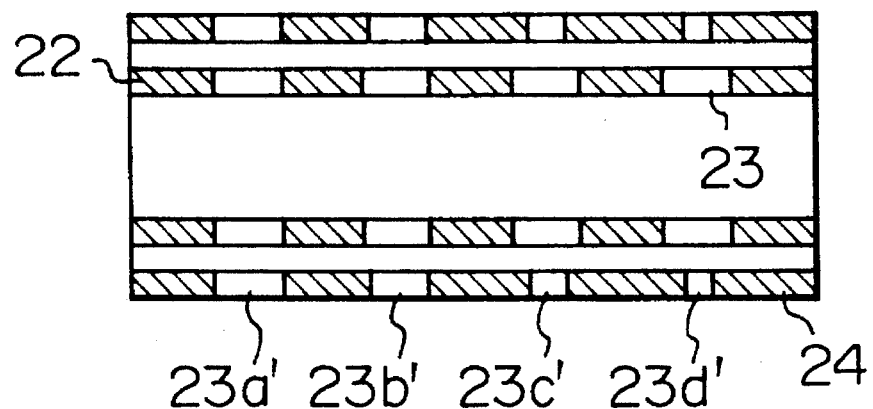
FIGS. 8 and 9 are views showing examples of the structure of the electrostatic lens for accelerating or decelerating ions in the direction of the center axis according to a third embodiment of the present invention.
Figure 9:
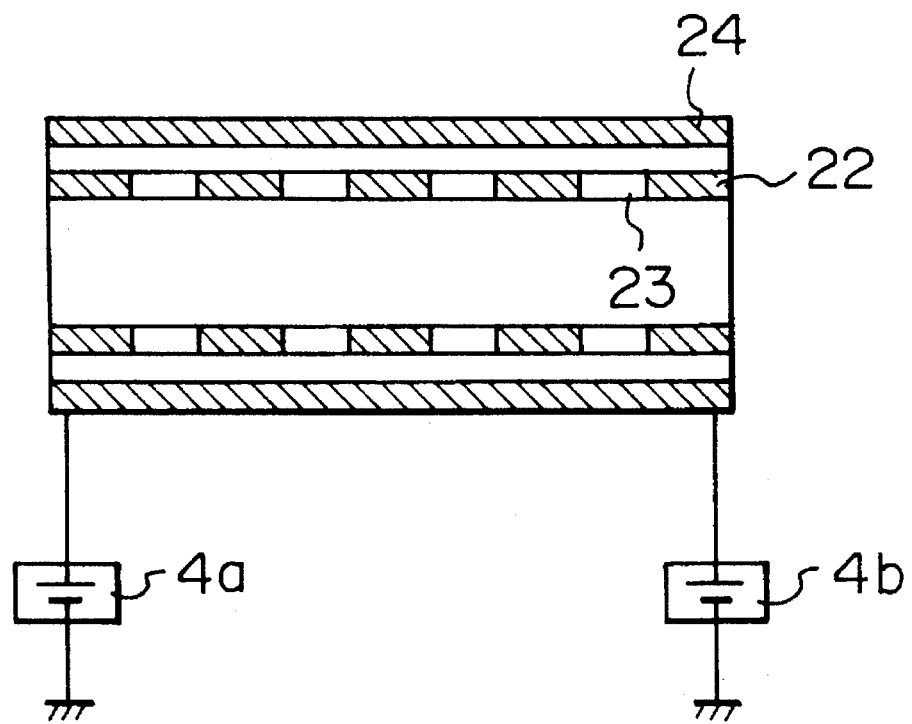

In the case where the intensity of electric field penetrating from the inner electrode of the electrostatic lens into the cylinder is changed to accelerate or decelerate ions to thereby change the focusing effect in the cylinder, the opening area of evacuation holes provided in the outer electrode may be changed in the direction along the center axis of the electrostatic lens. For example, FIG. 8 shows a structure for decelerating ions in the direction of the axis. When the respective opening areas of the holes 23'a, 23'b, 23'c and 23'd opened in the outer electrode 24 are reduced gradually along the center axis, the intensity of electric field penetrating into the cylinder of the inner electrode 22 changes in the direction of the center axis to thereby decelerate ions. Alternatively, different potentials may be applied to the opposite ends of the outer or inner electrode so that the intensity of electric field penetrating into the cylinder is changed in the direction of the axis by using the potential drop in the outer or inner electrode portion. FIG. 9 shows a structure in which voltages are applied to the opposite ends of the outer electrode 24 by power supplies 4a and 4b so that the axial gradient in the intensity of the electric field penetrating into the cylinder of the inner electrode 22 is changed arbitrarily by the voltage drop in the outer electrode 24. Here, the outer electrode 24 having the opposite ends supplied with the different voltages by the power supplies 4a and 4b is preferably formed of not a metal material but a resisting material to prevent excessive heating.

In the aforementioned structure, the electrostatic lens portion is preferably heated by a heater or the like to reduce the contamination of the electrostatic lens. Even in the case of an electrostatic lens which is constituted by a cylindrical inner electrode, an outer electrode located on in the outside of the inner electrode and has a plurality of holes at least in the inner electrode, at least one of the inner and outer electrodes is preferably heated by a heater or the like. Further, the electrode having the hole of the ion introducing aperture for introducing ions into the mass analysis region is also preferably heated.

(Fourth Embodiment)

Figure 10:
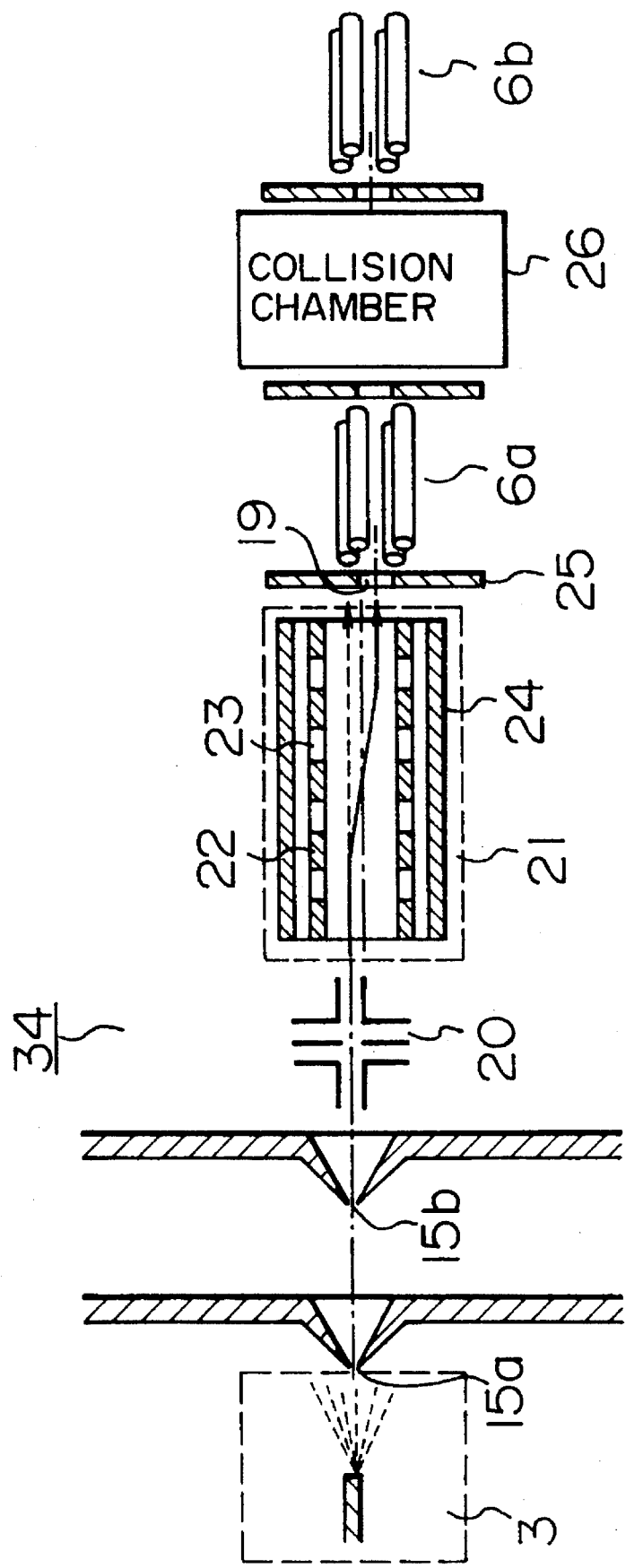
FIG. 10 is a view showing the structure of a mass spectrometer using a combination of a large number of mass analysis regions according to a fourth embodiment of the present invention.

FIG. 10 shows an embodiment of a mass spectrometer having a plurality of mass analysis regions arranged in multiple stages. After ions introduced through the ion sampling apertures 15a and 15b into the vacuum region 34 are separated from charged droplets or droplets without charge by the electrostatic lens 21, the ions are introduced to a first-stage mass analysis region 6a and are mass separated. The mass-separated ions to be analyzed are fed into a collision chamber 26. In the collision chamber 26, the ions collide with neutral gas and cleft into so-called fragment ions. The fragment ions are further introduced into a second-stage mass analysis region 6b and are mass analyzed. Even in the case of such a mass spectrometer having a plurality of mass analysis regions, the structure in which an electrostatic lens for deflecting ions is arranged between the ion sampling aperture and the first-stage mass analysis region is effective. The respective center axes of the ion sampling apertures, electrostatic lens, ion introducing aperture and first-stage mass analysis region 6a are arranged in the same manner as in the first embodiment.

(Fifth Embodiment)

Figure 11:
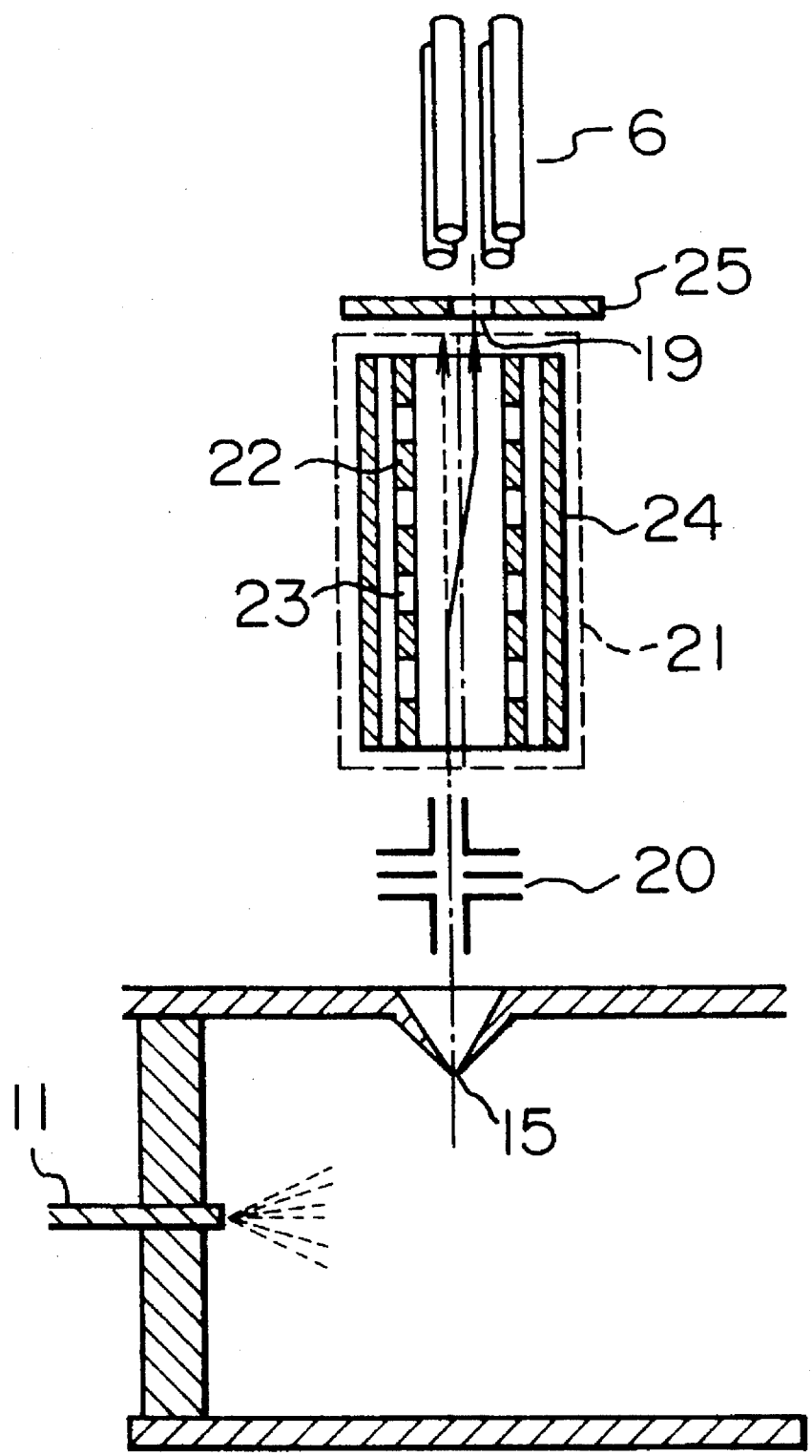
FIG. 11 is a view showing the structure of a thermospray mass spectrometer according to a fifth embodiment of the present invention.

FIG. 11 shows an embodiment of a mass spectrometer using a so-called thermospray method in which a sample solution is sprayed into a low pressure region. The effluent from the liquid chromatograph is introduced into a nebulization capillary 11 having an end arranged under a vacuum evacuated to the order of hundreds of Pa and being heated to about 200° C. and then nebulized. Sample molecule ions statistically charged by nebulization are introduced into the mass analysis region 6 evacuated to vacuum, through the ion sampling aperture 15 which is arranged perpendicular to the direction of nebulization. After the ions introduced through the ion sampling aperture 15 are accelerated by the extracting electrode 20, the ions are deflected by the electrostatic lens 21, introduced into the quadrupole mass analysis region 6 and mass analyzed. At the same time, charged droplets or droplets without charge, introduced together with the ions through the ion sampling aperture 15, move on an orbit represented by the broken line in the electrostatic lens and collide with the electrode 25 having the ion introducing aperture 19 opened therein. Accordingly, the charged droplets or droplets without charge are prevented from flowing into the mass analysis region 6. The respective center axes of the ion sampling aperture, electrostatic lens, ion introducing aperture and mass analysis region are arranged in the same manner as in the first embodiment.

(Sixth Embodiment)

Figure 12:
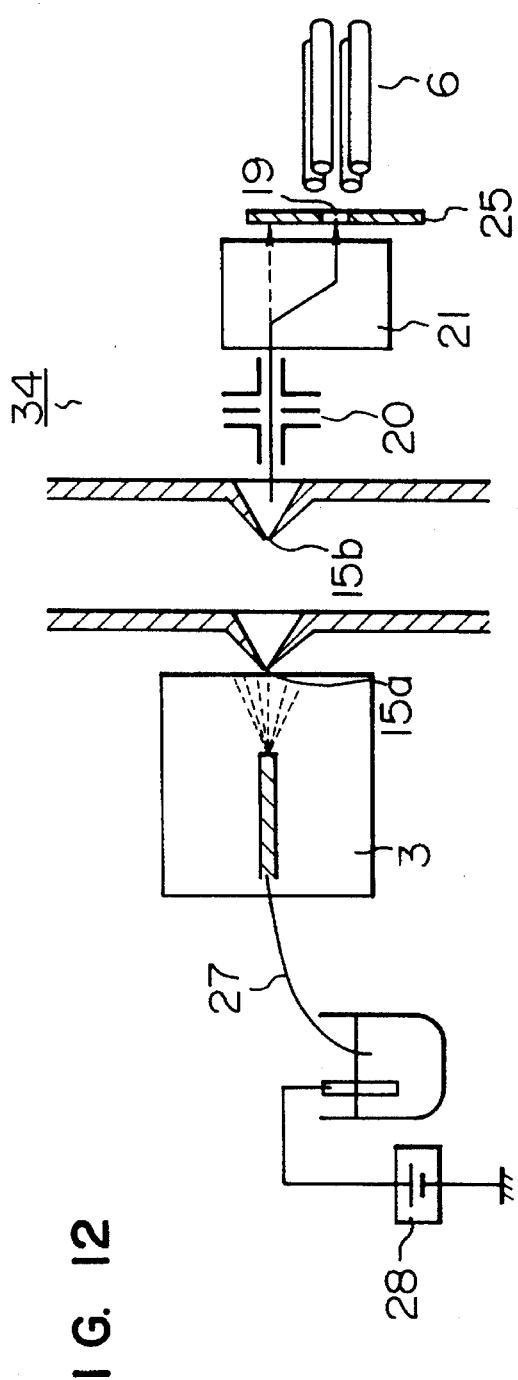
FIG. 12 is a view showing the structure of a capillary electrophoresis/mass spectrometer according to a sixth embodiment of the present invention.

As the mixture separating means, not only may liquid chromatography be used, but also capillary electrophoresis, supercritical fluid chromatography, etc. FIG. 12 shows a structure in which capillary electrophoresis is used as the separating means. A sample introduced to an end of a capillary 27 is electrically floated in the capillary 27 by a high voltage applied between opposite ends of the capillary 27 by a power supply 28 for electrophoresis. The sample which has reached the terminal end of the capillary 27 is introduced into the ion source 3 and ionized (one end of the capillary 27 is connected to the ion source). The generated ions are introduced through the ion sampling apertures 15a and 15b into a vacuum region 34, in which the ion orbit is deflected (as represented by the solid line in the electrostatic lens 21) by the electrostatic lens 21 and then mass-separated by the mass analysis region 6. At this time, charged droplets or droplets without charge, derived from a buffer solution or the like, are hardly deflected by the electric field of the electrostatic lens 21 (as represented by the broken line in the electrostatic lens 21), so that the droplets never reach the mass analysis region 6.

In the capillary electrophoresis method, there are proposed various modes such as capillary zone electrophoresis using free solvent in a capillary, capillary gel electrophoresis in which a capillary is filled with gel, micellar electrokinetic chromatography using difference of partition of samples into micelle, isotacho-isoelectric focusing electrophoresis in which samples are introduced to an interface of solvent containing ions different in mobility and arranged in the order of the mobility of the samples, and so on. It is a matter of course that the present invention is effective not only for the mode of capillary electrophoresis but also for the other respective modes.

(Seventh Embodiment)

Figure 13:
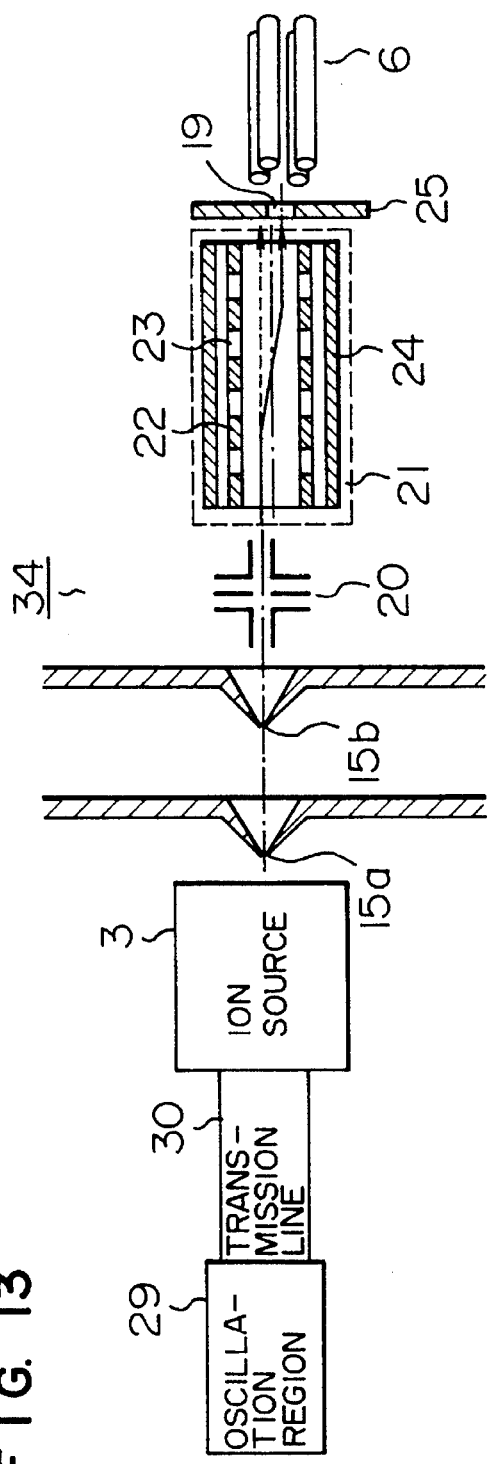
FIG. 13 is a view showing the structure of a mass spectrometer in which ions are generated in plasma according to a seventh embodiment of the present invention.

FIG. 13 shows an example of the structure of a mass spectrometer which is different from the mass spectrometer for analyzing a mixture in solution but has an inductively coupled plasma source or a microwave-induced plasma source. High-frequency electromagnetic wave such as microwave obtained from an oscillator 29 is introduced through a transmission line 30 into the ion source 3. A resonator is provided in the ion source 3 so that a plasma state is generated by discharging in the resonator. The sample is introduced into the plasma, ionized and then introduced through the ion sampling apertures 15a and 15b into the vacuum region 34. If photons such as ultraviolet rays obtained by discharging reach the ion detector at this time, the photons are detected as noise. Only ions are deflected (as indicated by the solid line in the electrostatic lens 21) by the electrostatic lens 21 so that the ions can reach the mass analysis region 6, whereas photons move straight (as represented by the broken line in the electrostatic lens 21) and collide with the electrode 25 having the hole of the ion introducing aperture 19 so that the photons are eliminated. Accordingly, the sensitivity of the mass spectrometer having the inductively coupled plasma source or microwave-induced plasma source can be improved by the present invention. The respective center axes of the ion sampling apertures, electrostatic lens, ion introducing aperture and mass analysis region are arranged in the same manner as in the first embodiment.

(Eighth Embodiment)

Figure 14:
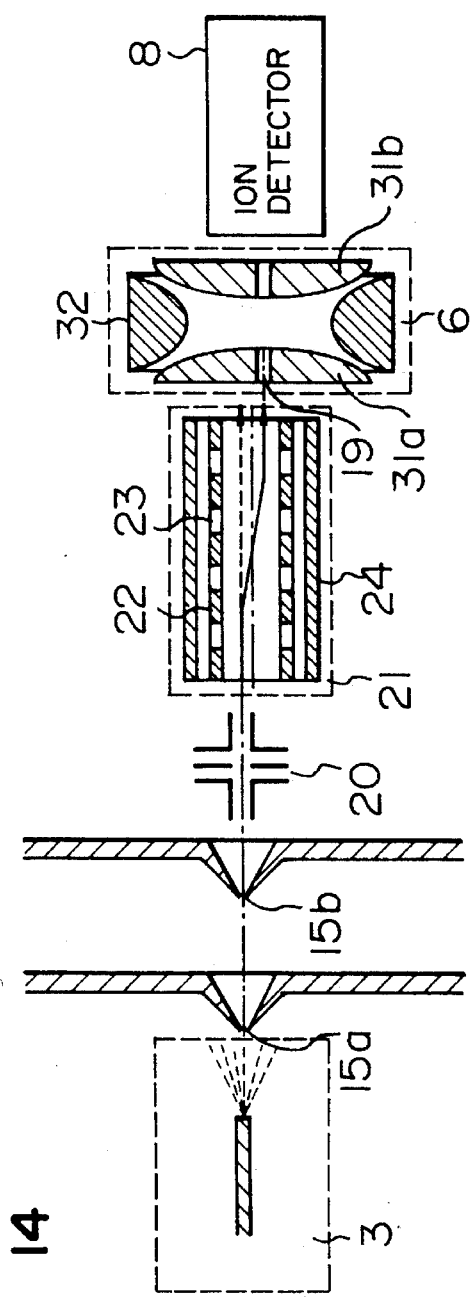
FIGS. 14 and 15 are views showing the structure of a mass spectrometer having an ion trap mass analysis region according to an eighth embodiment of the present invention.

The present invention is also effective for a mass spectrometer using mass analysis regions other than the quadrupole mass analysis region. FIG. 14 shows an example of the structure of a mass spectrometer having an ion trap mass analysis region. In the ion trap mass analysis region 6, ions are enclosed in a narrow space by a high-frequency electric field and analyzed. As shown in FIG. 14, the ion trap mass analysis region 6 is constituted by the following three electrodes: two electrodes 31a and 31b called "endcap electrodes" and a ring electrode 32 which is disposed so as to surround the endcap electrodes. Ions introduced through the ion sampling aperture into a vacuum are accelerated by the extracting electrode 20 and then deflected by the electrostatic lens 21. Then, the ions are guided into the ion trap by the endcap electrode 31a having the ion introducing aperture 19 opened therein.

In the ion trap, the ion orbit is controlled on the basis of the DC/AC electric field given by the endcap electrodes 31a and 31b and the ring electrode 32, so that only the ions having specific mass are enclosed. The enclosed ions are withdrawn from the endcap electrode 31b in accordance with the potential pulsatorily given to the endcap electrodes 31a and 31b at the opposite ends and detected by the ion detector 8. In the ion trap mass analysis region 6, mass analysis is performed in a closed space. If charged droplets or droplets without charge flow into the mass analysis region 6, the ring electrode 32 is contaminated with the charged droplets or droplets without charge. Because the ion trap mass analysis region 6 in FIG. 14 has a closed structure, the degree of contamination of the ring electrode 32 is relatively large compared with the quadrupole mass analysis region 6 in FIG. 1. If the ring electrode 32 is contaminated, the analysis characteristic of the mass analysis region 6 is changed to make long-term stable mass analysis difficult. Accordingly, the structure in which only the ions are deflected and introduced into the ion trap is effective.

Figure 15:
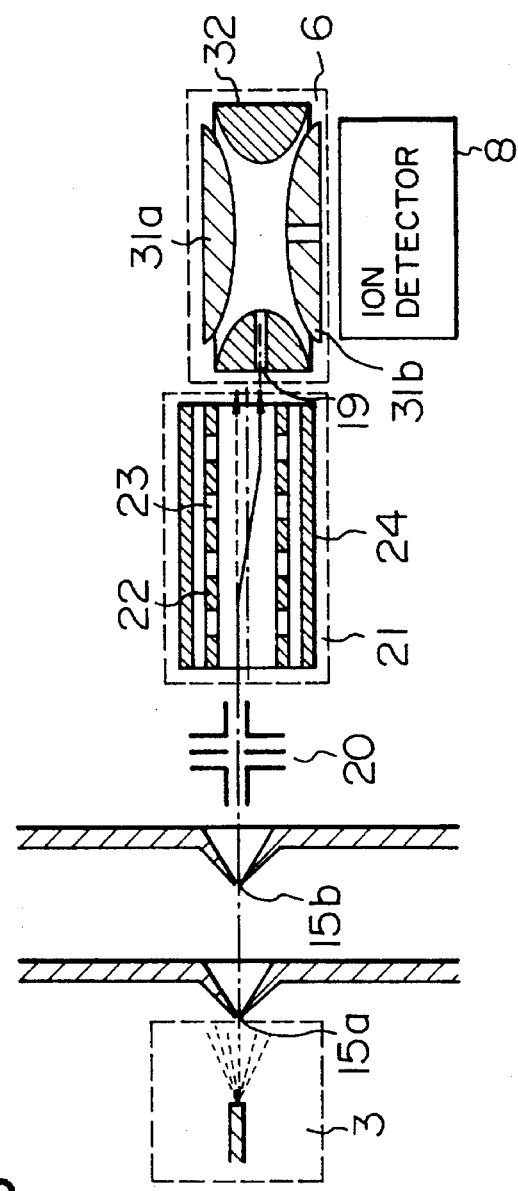

FIG. 15 shows a structure in which the ion introducing aperture 19 is provided in the ring electrode 32 in the ion trap mass spectrometer. Also in this case, the same effect as obtained by the apparatus shown in FIG. 14 can be obtained. Also in the ion trap mass analysis region, the endcap electrode or ring electrode having opening of the ion introducing aperture 19 is preferably heated by a heater or the like to reduce contamination with charged droplets or droplets without charge. In FIGS. 14 and 15, the respective center axes of the ion sampling apertures, electrostatic lens, ion introducing aperture and mass analysis region are arranged in the same manner as in the first embodiment.

A modified example of the structure shown in FIG. 14 will be described below. In the structure of FIG. 14, the respective center axes of the ion sampling apertures, electrostatic lens, ion introducing aperture and mass analysis region do not overlap each other. The same effect as obtained by the apparatus shown in FIG. 14 can be obtained by a structure in which: the center axis of the ion introducing aperture is arranged so as to be shifted from the center axis of the mass analysis region; the respective center axes of the ion sampling apertures and mass analysis region are arranged so as to be coincident with each other; and the respective center axes of the electrostatic lens, ion sampling apertures and ion introducing aperture are arranged so as to be shifted from each other.

(Ninth Embodiment)

Figure 16:
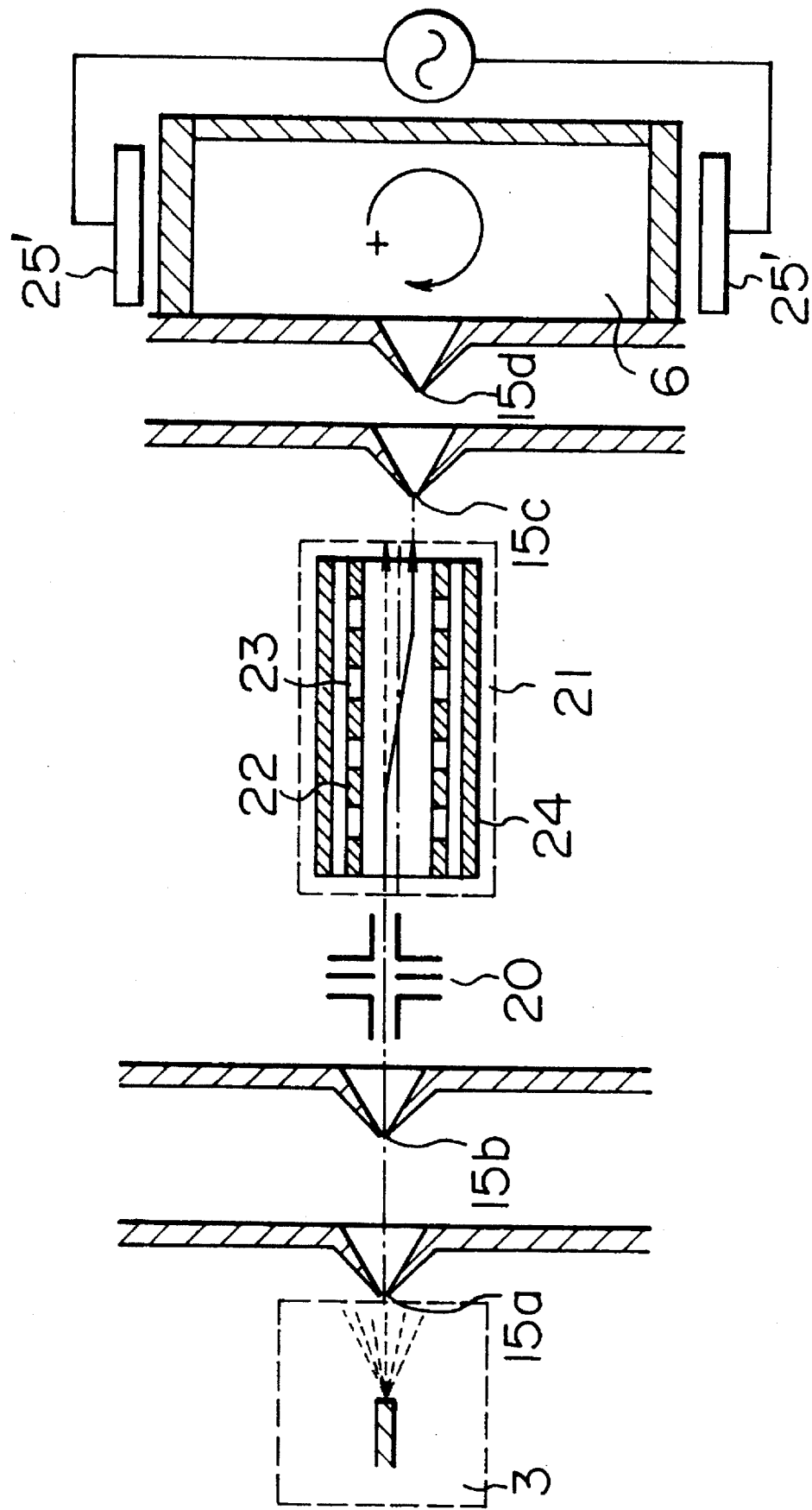
FIG. 16 is a view showing the structure of a mass spectrometer having a Fourier transformation ion cyclotron resonance mass analysis region according to a ninth embodiment of the present invention.

FIG. 16 shows an example of the structure of a mass spectrometer having a Fourier transformation ion cyclotron resonance mass analysis region as the mass analysis region 6. Fourier transformation ion cyclotron resonance mass spectrometry is a method in which: ions are cyclotron-moved under very low pressure and an intensive magnetic field; the rotating frequency of the ions is detected by an electrode 25' located outside of a vacuum container; and the mass of the ions is determined by Fourier transformation of the frequency spectra thereof. This method has very high resolution but the mass analysis region requires a high degree of vacuum of from $10^{-6}$ Pa to $10^{-7}$ Pa. In the case where ions are introduced from atmospheric air, therefore, not only a plurality of ion sampling apertures 15a, 15b, 15c and 15d must be provided but also large-sized vacuum pumps of a high evacuating speed type must be used as vacuum systems for evacuating a space between the ion sampling apertures 15a and 15b, a space between the ion sampling apertures 15b and 15c, and a space between the ion sampling apertures 15c and 15d, respectively. The method in which ions are separated from charged droplets or droplets without charge by deflection of the ions and successively introduced into the next-stage ion sampling aperture, as shown in FIG. 16, is effective because the degree of vacuum in the mass analysis region can be prevented from being deteriorated by the inflow of the charged droplets or droplets without charge.

Figure 17:
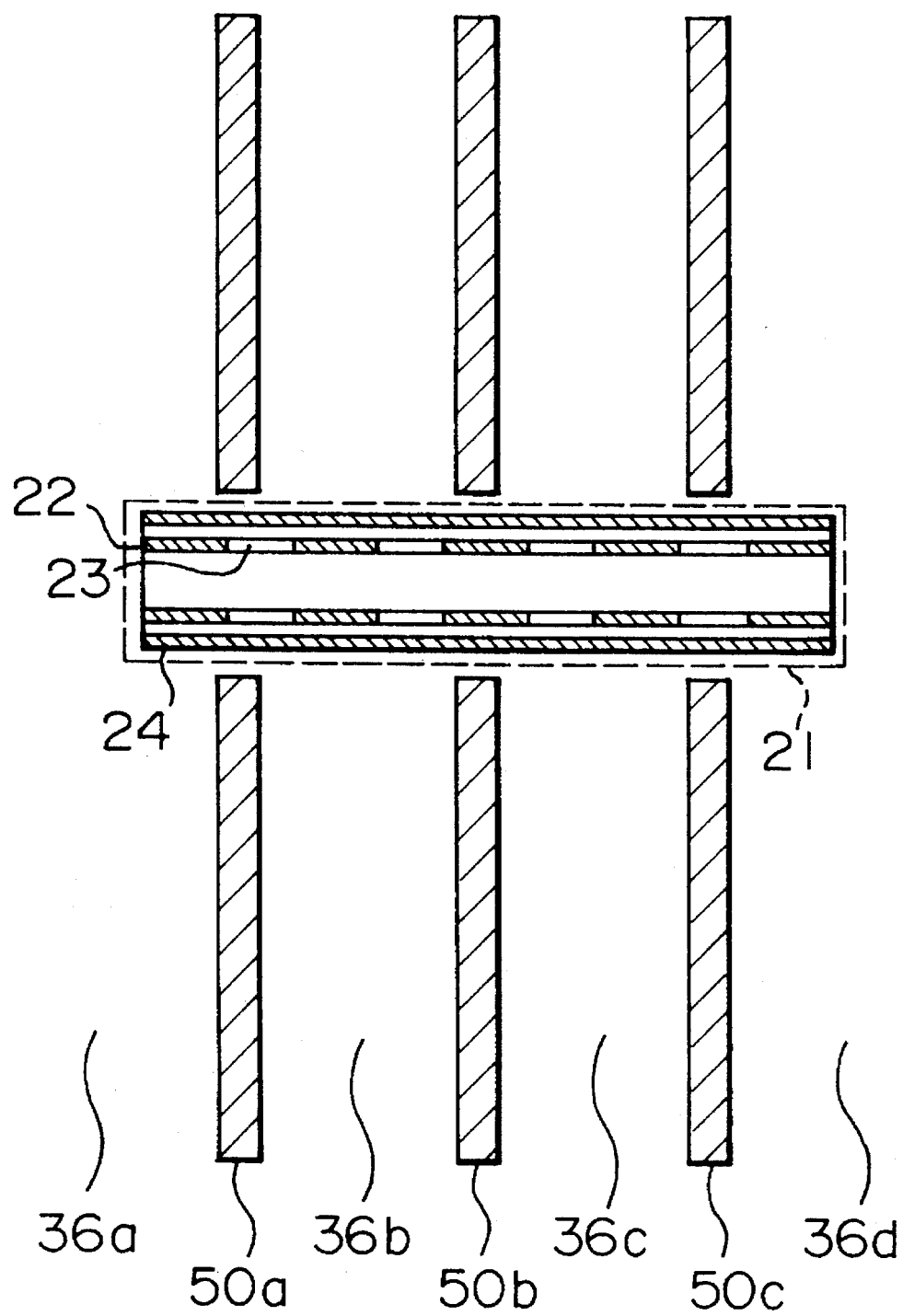
FIG. 17 is a view showing a structure in which the present invention is adapted to a mass spectrometer having a Fourier transformation ion cyclotron resonance mass analysis region.

Besides the aforementioned Fourier transformation ion cyclotron mass spectrometer, a structure in which a cylindrical electrostatic lens 21 having holes 23 in an inner electrode 22 is laid over a plurality of vacuum regions 36a, 36b, 36c and 36d which differ in the degree of vacuum and which are separated by walls 50a, 50b and 50c as shown in FIG. 17 is effective for efficient transportation of ions to a very low pressure region. In the apparatuses shown in FIGS. 1 through 7 and FIGS. 10 through 16, the extracting electrode 20 is not needed, particularly when the electrostatic lens 21 has the effect of introducing ions into the electrostatic lens on the basis of the electric field.

Figure 18:
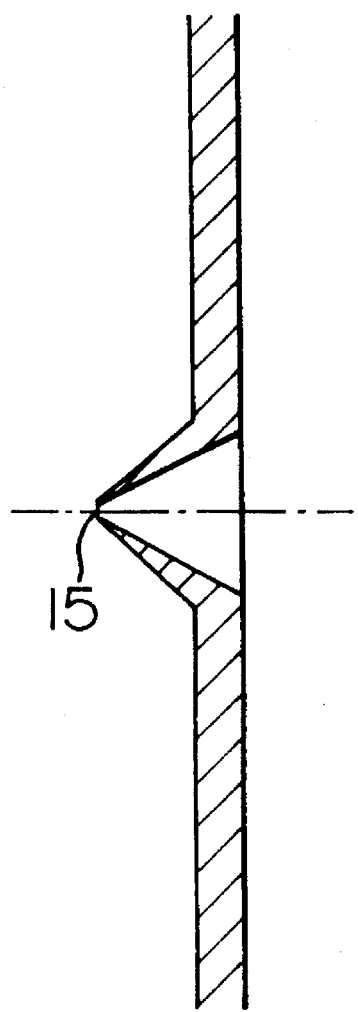
FIGS. 18 and 19 are enlarged views of ion sampling apertures, respectively.
Figure 19:
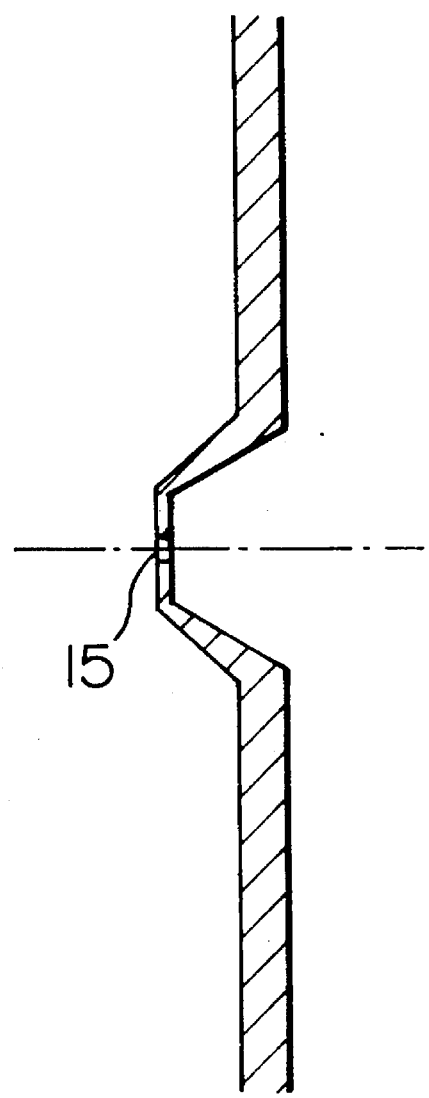
Figure 20A:
Figure 20B:
Figure 20C:
Figure 20D:
Figure 23:
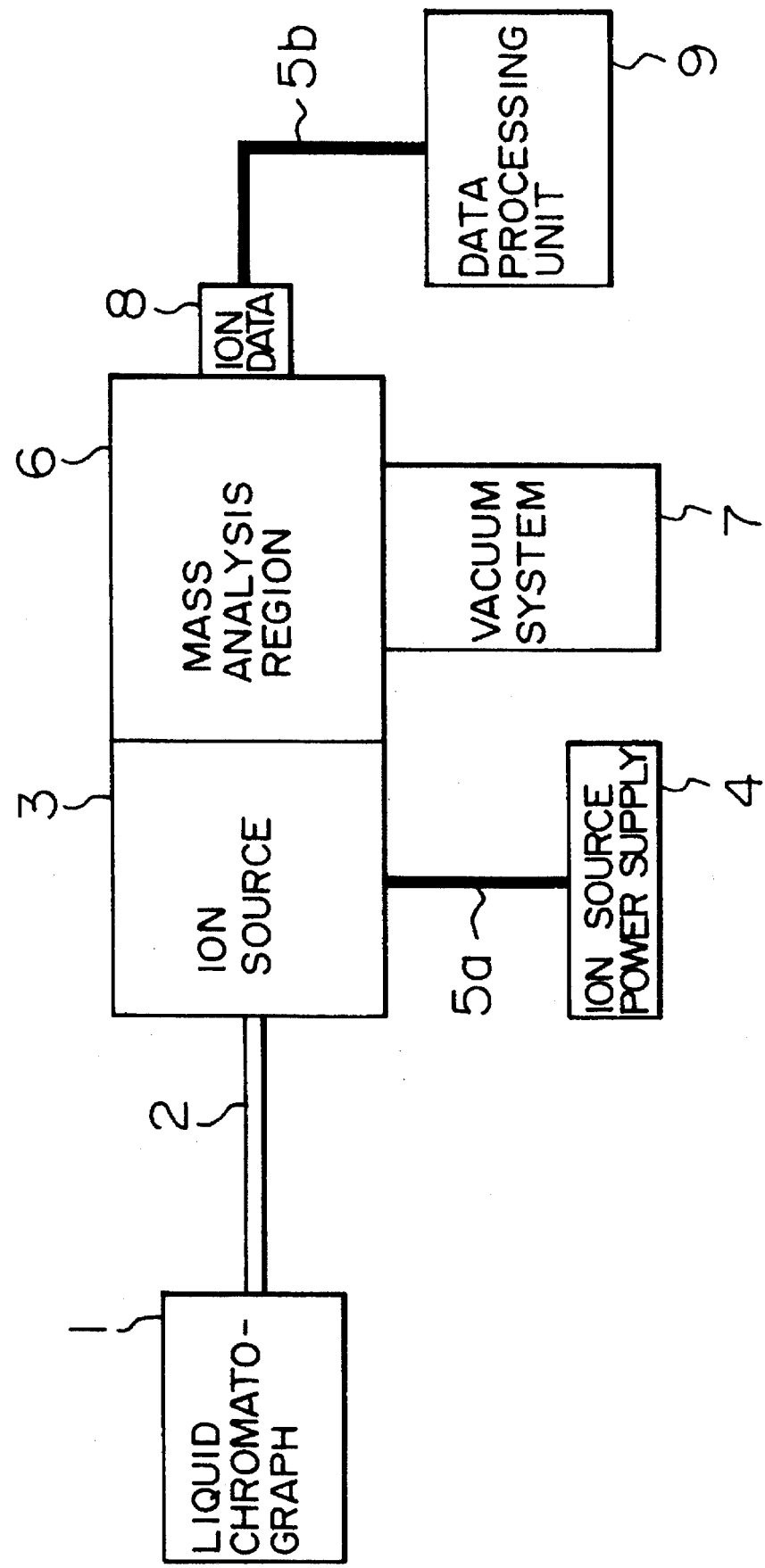
FIG. 23 is a view showing the structure of a conventional liquid chromatograph/mass spectrometer.
Figure 24:
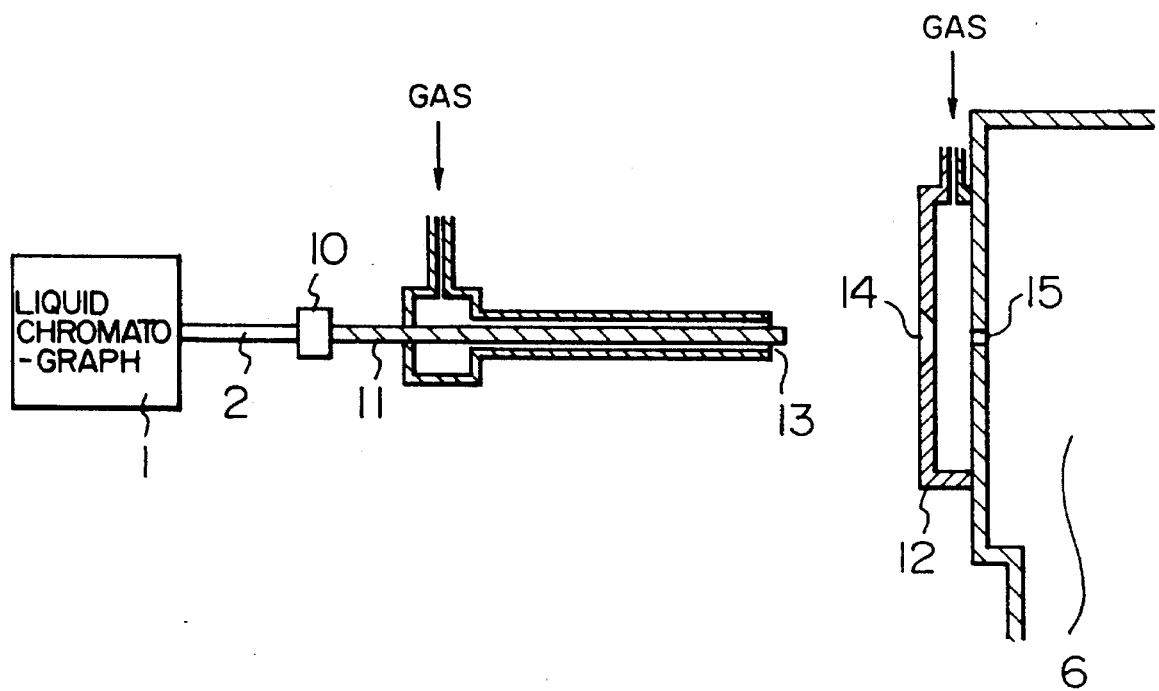
FIG. 24 is a sectional view showing the structure of a liquid chromatograph/mass spectrometer using a conventional electrospray method.
Figure 25:
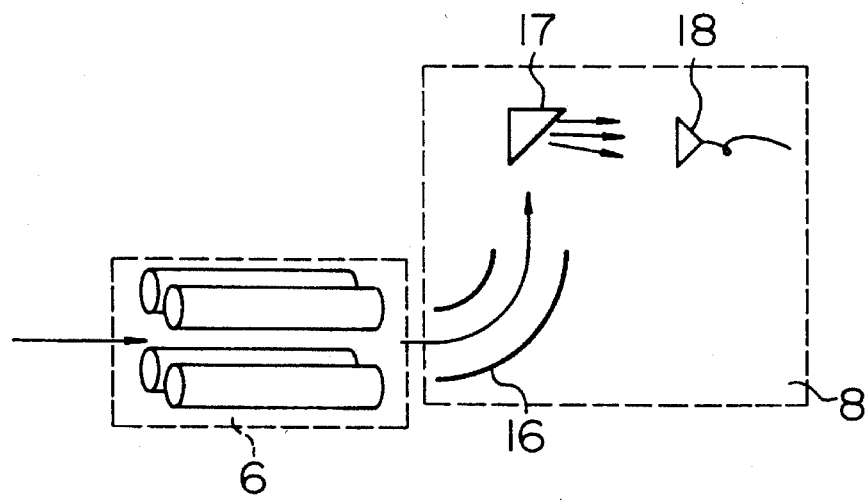
FIG. 25 is a view showing the structure of an ion detector used in a conventional liquid chromatograph/mass spectrometer.

The definition of the center axis of the ion sampling aperture in the present invention will be described with care. The ion sampling aperture 15 is preferably shaped like a taper as shown in FIG. 18. Because it is difficult to process, however, a hole having a predetermined shape such as a circular shape or a square shape is generally formed on a plane at the end portion as shown in FIG. 19. In the present invention, the center axis of the ion sampling aperture means an axis which passes through the center of the hole and makes a normal line to the plane at the end portion.

S/N in the apparatus according to the present invention will be described below.

In the structure in which the center axis of the ion sampling aperture 15b is made to be coincident with the center axis of the ion introducing aperture 19 for introducing ions into the quadrupole mass analysis region 6, the change with the passage of time, of a signal obtained from the mass spectrometer in which the value of mass/charge is 571 is measured by using the atmospheric pressure ionization mass spectrometer shown in FIG. 2 to thereby calculate noise level. FIGS. 20A–20D show results of measurement of noise level. Conditions for measurement are as follows.

Ionization Method: electrospray method

Solution: water/methanol (50/50)

Flow Rate: 100, 80, 60 and 40 µl/min as four kinds

Measured Value of Mass/Charge: m/z=571

FIGS. 21A–21D show results of measurement of noise level in the case where the center axis of the ion sampling aperture 15b shown in FIG. 2 and the center axis of the ion introducing aperture 19 in the atmospheric pressure ionization mass spectrometer are 4 mm shifted from each other. Conditions for measurement are equal to the aforementioned conditions.

In FIGS. 20A–20D, spike noise, derived from the charged droplets or droplets without charge entering into the quadrupole mass analysis region 6, appears frequently. In FIGS. 21A–21D, there is no appearance of spike noise derived from the charged droplets or droplets without charge, at any flow rate. As is obvious from comparison between FIGS. 20A–20D and 21A–21D, noise is reduced extremely when the center axis of the ion sampling aperture and the center axis of the ion introducing aperture are arranged so as to be shifted from each other. In FIGS. 20A–20D, the frequency of generation of spike noise increases as the solution flow rate increases. In FIGS. 21A–21D, however, spike noise is inconspicuous even in the case where the solution flow rate changes.

When noise levels from the results of measurement in FIGS. 20A–20D and 21A–21D are compared with each other on the basis of the maximum value of spike noise, the noise level is reduced to a value not larger than about one tenth the noise level by shifting these center axes. Accordingly, the shifting of the center axis of the ion sampling aperture and the center axis of the ion introducing aperture from each other is very effective for reduction of noise.

On the other hand, the shifting of these axes substantially reduces the signal intensity. FIG. 22 shows the relative ion strength (transmittivity) of divalent ions $(M+2H)^{2+}$ (mass/charge=571) of gramicidin S obtained in the case where the difference between the center axis of the ion sampling aperture 15b and the center axis of the ion introducing aperture 19 in FIG. 2 is changed to 0 mm, 4 mm and 10 mm, successively. Experimental conditions used herein are as follows.

Ionization Method: electrospray method

Solution: water/methanol (50/50)

Sample Solution and its Concentration:

gramicidin S ($10^{-6}$M)

Solution Flow Rate: 40 µl/min

Measured Value of Mass/Charge: m/z=571

In any case of data shown in FIGS. 20, 21 and 22, the length in the direction of the center axis of the electrostatic lens 21 for deflecting the ion orbit is 104 mm.

As shown in FIG. 22, the quantity of the signal is reduced to about 80 when the difference between the center axis of the ion sampling aperture and the center axis of the ion introducing aperture is 4 mm, whereas the quantity of the signal is reduced to about 50 when the difference is 10 mm (the ion strength obtained in the case of no difference between the two center axes is regarded as 100).

As described above, by 4 mm offsetting the two center axes from each other to eliminate the influence of the charged droplets or droplets without charge, the noise level is reduced to a value not larger than about one tenth the noise level but the quantity of the signal is reduced to about four fifth. As a result, S/N is improved by a factor not smaller than about eight times in total.

According to the present invention, not only is the mass analysis region prevented from being contaminated but the charged droplets or droplets without charge are prevented from entering as a noise source into the mass analysis region, so that ions can be analyzed efficiently. Accordingly, the long-term stable operation of the mass spectrometer can be made, and the mass spectrometer can be provided as a noiseless high-sensitive mass spectrometer. That is, the S/N is improved by a factor not smaller than eight times, so that the sensitivity in the mass spectrometer is improved by about one order of magnitude.

We claim:

1. A mass spectrometer comprising:

an ionization region for ionizing a sample under atmosphere pressure;

an ion sampling aperture for introducing ions generated in said ionization region into a vacuum; and a mass analysis region for mass analyzing said ions on the basis of a high-frequency electric field, wherein:

an electrostatic lens for deflecting a direction of movement of said ion from a center axis of said ion sample aperture is arranged between said ionization region and said mass analysis region; and a center axis of an aperture for introducing ions into said mass analysis region and the center axis of said ion sample aperture are arranged in parallel and offset from each other.

2. A mass spectrometer according to claim 1, wherein:

said electrostatic lens is constituted by a cylindrical inner electrode and an outer electrode arranged on the outside of said inner electrode; and the center axis of said ion sampling aperture and a center axis of a cylindrical inner electrode constituting said electrostatic lens are arranged in parallel and offset from each other.

3. A mass spectrometer according to claim 1, wherein:

said electrostatic lens is constituted by a cylindrical inner electrode and an outer electrode arranged on the outside of said inner electrode; and holes are formed in an outer circumferential surface of a cylinder constituting said inner electrode.

4. A mass spectrometer according to claim 1, wherein:

said electrostatic lens is constituted by a cylindrical inner electrode and an outer electrode arranged on the outside of said inner electrode; and holes are formed in respective outer circumferential surfaces of cylinders constituting said inner electrode and said outer electrode.

5. A mass spectrometer according to claim 1, wherein:

said electrostatic lens is constituted by a cylindrical inner electrode and an outer electrode arranged on the outside of said inner electrode;

multiple holes are formed in respective outer circumferential surfaces of cylinders constituting said inner electrode and said outer electrode; and a respective opening areas of said holes in said outer electrode are changed in the direction along a center axis of said electrostatic lens so that the intensity of the electric field penetrating from said holes of said inner electrode into the cylinder constituting said inner electrode is changed in the direction along the center axis of said electrostatic lens.

6. A mass spectrometer according to claim 1, wherein:

said electrostatic lens is constituted by a cylindrical inner electrode and an outer electrode arranged on the outside of said inner electrode; and different potentials are applied to opposite ends in the direction along a center axis of at least one of said inner and outer electrodes to give a voltage drop between said opposite end of the electrode so that the intensity of the electric field penetrating into the cylinder constituting said inner electrode is changed in the direction along a center axis of said electrostatic lens.

7. A mass spectrometer according to claim 1, wherein said electrostatic lens is constituted by a cylindrical inner electrode and an outer electrode arranged on the outside of said inner electrode; and at least one of said inner and outer electrodes is formed of an electrically conductive resin.

8. A mass spectrometer according to claim 1, wherein said electrostatic lens is constituted by a cylindrical inner electrode and an outer electrode arranged on the outside of said inner electrode; and at least one of said inner and outer electrodes is formed of an electrically conductive film formed on a surface of an insulating material.

9. A mass spectrometer according to claim 1, wherein said electrostatic lens is constituted by a cylindrical inner electrode and an outer electrode arranged on the outside of said inner electrode; and said outer electrode is formed of metal meshes.

10. A mass spectrometer according to claim 1, further comprising means for heating said electrostatic lens.

11. A mass spectrometer according to claim 1, wherein:

said mass analysis region is constituted by a selected one of a quadrupole mass spectrometer, an ion trap mass spectrometer and an ion cyclotron resonance mass spectrometer.

12. A mass spectrometer according to claim 1, wherein said sample is supplied from selected one of an end of a column in liquid chromatography, an end of a capillary in capillary electrophoresis and an end of a column in supercritical fluid chromatography.

13. A mass spectrometer comprising:

an ionization region for ionizing a sample under atmospheric pressure;

an ion sampling aperture for introducing ions generated in said ionization region into a vacuum; and a mass analysis region for mass analyzing said ions on the basis of a high-frequency electric field, wherein:

an electrostatic lens for deflecting a direction of movement of said ion from a center axis of said ion sampling aperture in arranged between said ionization region and said mass analysis region; and a center axis of an aperture for introducing ions into said mass analysis region and the center axis of said ion sampling aperture intersect.

14. A mass spectrometer according to claim 13, wherein:

a center axis of a cylindrical inner electrode constituting said electrostatic lens has curvature.

15. A mass spectrometer according to claim 13, wherein:

the center axis of said ion sampling aperture and a center axis of a cylindrical inner electrode constituting said electrostatic lens intersect.

16. A mass spectrometer comprising:

an ionization region for ionizing a sample under atmospheric pressure;

an ion sampling aperture for introducing ions generated in said ionization region into a vacuum; and a mass analysis region for mass analyzing said ions on the basis of a high-frequency electric field, wherein:

an electrostatic lens for deflecting a direction of movement of said ion from a center axis of said ion sampling aperture is arranged between said ionization region and said mass analysis region; and a center axis of an aperture for introducing ions into said mass analysis region and the center axis of said ion sampling aperture are arranged in by parallel and offset from each other and so that projection of said ion sampling aperture onto a plane perpendicular to these center axes and projection of said ion introducing aperture onto said plane do not overlap each other.

17. A mass spectrometer comprising:

a nebulization ion source in which an effluent introduced from a liquid chromatograph into one end of a capillary is nebulized from the other end of said capillary to thereby generate ions;

an ion sampling aperture for introducing the generated ions into a vacuum;

a quadrupole mass spectrometer for mass analyzing said ions on the basis of a high-frequency electric field; and an electrostatic lens arranged between said nebulization ion source and said quadrupole mass spectrometer for deflecting a direction of movement of said ions from a center axis of said ion sampling aperture, wherein:

said electrostatic lens is constituted by a cylindral inner electrode and a cylindrical outer electrode arranged on the outside of said inner electrode;

holes are formed at least in a surface of a cylinder constituting said inner electrode; and a center axis of an aperture for introducing ions into said quadrupole mass spectrometer and the center axis of said ion sampling aperture are arranged in by parallel and offset from each other.

18. A mass spectrometer comprising:

a nebulization ion source in which an effluent introduced from a liquid chromatograph into one end of a capillary is nebulized from the other end of said capillary to thereby generate ions;

an ion sampling aperture for introducing the generated ions into a vacuum;

an ion trap mass spectrometer for enclosing said ions on the basis of a high-frequency electric field; and an electrostatic lens disposed between said nebulization ion source and said ion trap mass spectrometer or for deflecting a direction of movement of said ions from a center axis of said ion sampling aperture, wherein:

said electrostatic lens is constituted by a cylindrical inner electrode and a cylindrical outer electrode arranged on the outside of said inner electrode;

holes are formed at least in an outer circumferential surface of a cylinder constituting said inner electrode; and a center axis of an aperture for introducing ions into said ion trap mass spectrometer and the center axis of said ion sampling aperture are arranged in parallel and offset from each.

19. A mass spectrometer comprising:

an ion source for generating plasma and for introducing a sample into the plasma to thereby generate ions;

an ion sampling aperture for introducing the generated ions into a vacuum;

a mass analysis region for mass analyzing said ions on the basis of a high-frequency electric field; and an electrostatic lens disposed between said ion source and said mass analysis region for deflecting a direction of movement of said ions from a center axis of said ion sampling aperture, wherein:

said electrostatic lens is constituted by a cylindrical inner electrode and a cylindrical outer electrode arranged on the outside of said inner electrode;

holes are formed at least in an outer circumferential surface of a cylinder constituting said inner electrode; and a center axis of an aperture for introducing ions into said mass analysis region and the center axis of said ion sampling aperture are arranged in parallel and offset from each other.

20. A mass spectrometer comprising:

an ionization region for ionizing a sample under atmospheric pressure;

an ion sampling aperture for introducing ions generated in said ionization region into a vacuum;

a Fourier transformation ion cyclotron resonance mass spectrometer for making said ions rotate in an intensive magnetic field to thereby mass analyze said ions on the basis of the rotational frequency of said ions; and an electrostatic lens arranged between said ionization region and said mass spectrometer for deflecting a direction of movement of said ion from a center axis of said ion sampling aperture; wherein:

said electrostatic lens is constituted by a cylindrical inner electrode and a cylindrical outer electrode arranged on the outside of said inner electrode;

holes are formed at least in an outer circumferential surface of a cylinder constituting said inner electrode; and a center axis of an aperture for introducing ions into said mass spectrometer and the center axis of said ion sampling aperture are arranged in parallel and offset from each other.

21. A mass spectrometer, comprising:

an ionization region for ionizing a sample under atmospheric pressure;

a first aperture for introducing ions generated in said ionization region into an intermediate pressure region;

a second aperture for introducing said ions into a vacuum region from said intermediate pressure region;

a mass analysis region for mass analyzing said ions on the basis of a high-frequency electric field, said mass analysis region being arranged in said vacuum region;

a third aperture for introducing said ions passing through said second aperture into said mass analysis region; and an electrostatic ion deflecting lens for deflecting a direction of movement of said ions from the center of axis of said second aperture, said electrostatic ion deflecting lens being arranged between said second aperture and said third aperture in said vacuum region;

wherein a center axis of said third aperture and a center axis of said second aperture are arranged in parallel and offset from each other.

22. A mass spectrometer according to claim 21, wherein said electrostatic ion lens is constituted by a cylindrical inner electrode and an outer electrode arranged on the outside of said inner electrode.

23. A mass spectrometer according to claim 21, wherein said electrostatic ion lens is constituted by a cylindrical inner electrode and a cylindrical outer electrode arranged on the outside of said inner electrode.

24. A mass spectrometer according to claim 22 or claim 23, wherein the axial length of said inner electrode is larger than the inner diameter of said inner electrode.

25. A mass spectrometer, comprising:
an ionization region for ionizing a sample under atmospheric pressure;
a first aperture for introducing ions generated in said ionization region into an intermediate pressure region;
a second aperture for introducing said ions into a vacuum region from said intermediate pressure region;
a mass analysis region for analyzing said ions on the basis of a high-frequency electric field, said mass analysis region being arranged in said vacuum region;
a third aperture for introducing said ions passing through said second aperture into said mass analysis region; and
an electrostatic ion deflecting lens for deflecting a direction of movement of said ions from the center axis of said second aperture, said electrostatic ion deflecting lens being arranged between said second aperture and said third aperture in said vacuum region;
wherein a center axis of said third aperture and a center axis of said second aperture intersect.

26. A mass spectrometer according to claim 25, wherein said electrostatic ion lens is constituted by a cylindrical inner electrode and an outer electrode arranged on the outside of said inner electrode.

27. A mass spectrometer, comprising:
an ionization region for ionizing a sample under atmospheric pressure;
a first aperture for introducing ions generated in said ionization region into an intermediate pressure region;
a second aperture for introducing said ions into a vacuum region from said intermediate pressure region;
a mass analysis region for mass analyzing said ions on the basis of a high-frequency electric field, said mass analysis region being arranged in said vacuum region;
a third aperture for introducing said ions passing through said second aperture in to said mass analysis region; and
an electrostatic ion deflecting lens for deflecting a direction of movement of said ions from the center axis of said second aperture, said electrostatic ion deflecting lens being arranged between said second aperture and said third aperture in said region;
wherein said electrostatic ion deflecting lens is constituted by a cylindrical inner electrode and an outer electrode arranged on the outside of said inner electrode.

28. A mass spectrometer according to claim 27, wherein the axial length of said inner electrode is larger than the inner diameter of said inner electrode.

29. A mass spectrometer according to claim 27, wherein the axial length of said inner electrode is larger than the inner diameter of said inner electrode.

30. A mass spectrometer, comprising:
an ionization region for ionizing a sample under atmospheric pressure;
a first aperture for introducing ions generated in said ionization region into an intermediate pressure region;
a second aperture for introducing said ions into a vacuum region from said intermediate pressure region;
a mass analysis region for mass analyzing said ions on the basis of a high-frequency electric field, said mass analysis region being arranged in said vacuum region;
a third aperture for introducing said ions passing through said second aperture into said mass analysis region; and
an electrostatic lens for deflecting a direction of movement of said ions and for focusing said ions, said electrostatic lens being arranged between said second aperture and said third aperture in said vacuum region;
wherein said electrostatic ion lens deflects the direction of movement of said ions from the center axis of said second aperture.

31. A mass spectrometer according to claim 30, wherein said electrostatic ion lens is constituted by a cylindrical inner electrode and an outer electrode arranged on the outside of said inner electrode.

32. A mass spectrometer according to claim 30, wherein said electrostatic ion lens is constituted by a cylindrical inner electrode and a cylindrical outer electrode arranged on the outside of said inner electrode.

33. A mass spectrometer according to claim 31 or claim 32, wherein the axial length of said inner electrode is large than the inner diameter of said inner electrode.

34. A mass spectrometer, comprising:
an ionization means for ionizing a sample under atmospheric pressure;
an ion sampling aperture for introducing ions generated by said ionization mans into a vacuum;
a mass analysis means for mass analyzing said ions on the basis of a high-frequency electric field in said vacuum; and
an electrostatic lens for deflecting a direction of movement of said ions, said electrostatic lens being arranged between said ion sampling aperture and said mass analysis means;
wherein said electrostatic ion lens deflects the direction of movement of said ions from the center of axis of said ion sampling aperture in said vacuum, and wherein center axis of an aperture for introducing said ions into said mass analysis means and the center axis of said ion sampling aperture are arranged in parallel and offset from each other.

35. A mass spctrometer according to claim 34, wherein said electrostatic ion lens is constituted by a cylindrical inner electrode and an outer electrode arranged on the outside of said inner electrode.

36. A mass spectrometer according to claim 34, wherein said electrostatic ion lens is constituted by a cylindrical inner electrode and a cylindrical outer electrode arranged on the outside of said inner electrode.

37. A mass spectrometer according to claim 35 or claim 36, wherein the axial length of said inner electrode is large than the inner diameter of said inner electrode.

38. A mass spectrometer, comprising:
an ionization region, wherein a sample may be ionized in said ionization region;
a mass analysis region, wherein the ions may be mass analyzed in said mass analysis region;
an electrostatic lens located between said ionization region and said mass analysis region.

39. A mass spectrometer according to claim 38, further comprising:
a first aperture for introducing ions into said mass analysis region having a center axis; and
a second aperture for sampling ions from said ionization region having its own center axis, wherein:
the center axis of said first aperture and the center axis of said second aperture are parallel and offset from each other.

40. A mass spectrometer according to claim 38, further comprising:

a first aperture for introducing ions into said mass analysis region having a center axis; and a second aperture for sampling ions from said ionization region having its own center axis, wherein:

the center axis of said first aperture and the center axis of said second aperture intersect.

41. A method for performing mass spectrometry, comprising:

(a) ionizing a sample;

(b) deflecting and focusing the ions using an electrostatic lens; and (c) mass analyzing said ions.

42. The method according to claim 41, wherein said deflecting step includes deflecting said ions from:

a path coinciding with the center axis of an aperture for introducing ions into mass analysis region;

to a path coinciding with the center axis of an aperture for sampling ions from ionization region, wherein:

said center axis of ion-introducing aperture and center axis of ion-sampling aperture are parallel and offset from each other.

43. The method according to claim 41, wherein said deflecting step includes deflecting said ions from:

a path coinciding with the center axis of an aperture for introducing ions into mass analysis region;

to a path coinciding with the center axis of an aperture for sampling ions from ionization region, wherein:

said center axis of ion-introducing aperture and center axis of ion-sampling aperture intersect.

* * * * *

UNITED STATES PATENT AND TRADEMARK OFFICE
CERTIFICATE OF CORRECTION

PATENT NO. : 5,481,107
DATED : 2 January 1996
INVENTOR(S) : Yasuaki TAKADA et al.

It is certified that error appears in the above-identified patent and that said Letters Patent is hereby corrected as shown below:

| Column | Line | |
|---|---|---|
| 2 | 14 | Change "(SIN)" to --(S/N)--. |
| 4 | 22 | After "method." delete "and". |
| 6 | 9 | After "because" insert --a--. |
| 6 | 42 | After "may" delete "be"; after "always" insert --be--. |
| 11 | 51 | Change "it" to --this shape--. |
| 13 | 1 | Change "fifth" to --fifths--. |
| 13 | 60 | Delete "a". |
| 14 | 11 | After "wherein" insert --:--. |
| 14 | 17 | After "wherein" insert --:--. |
| 14 | 24 | After "wherein" insert --:--. |

UNITED STATES PATENT AND TRADEMARK OFFICE
CERTIFICATE OF CORRECTION

PATENT NO. : 5,481,107

DATED : 2 January 1996

INVENTOR(S) : Yasuaki TAKADA et al.

It is certified that error appears in the above-identified patent and that said Letters Patent is hereby corrected as shown below:

| Column | Line | |
|---|---|---|
| 14 | 30 | After "comprising" insert --:--. |
| 14 | 37 | After "wherein" insert --:--. |
| 14 | 52 | After "aperture" change "in" to --is--. |
| 15 | 11 | Delete "by". |
| 15 | 37 | Delete "by". |
| 15 | 49 | Delete "or". |
| 18 | 18 | Change "large" to --larger--. |
| 18 | 25 | Change "mans" to --means--. |
| 18 | 35 | After "wherein" insert --the--. |
| 18 | 49 | Change "large" to --larger--. |

UNITED STATES PATENT AND TRADEMARK OFFICE
CERTIFICATE OF CORRECTION

PATENT NO. : 5,481,107
DATED : 2 January 1996
INVENTOR(S) : Yasuaki TAKADA et al.

It is certified that error appears in the above-identified patent and that said Letters Patent is hereby corrected as shown below:

| Column | Line | |
|---|---|---|
| 18 | 56 | After "lens" insert --which deflects said ions, said lens being--. |
| 19 | 19 | After "into" insert --a--. |
| 20 | 2 | After "from" insert --an--. |
| 20 | 12 | After "into" insert --a--. |
| 20 | 15 | After "from" insert --an--. |

Signed and Sealed this

Fourth Day of June, 1996

Attest:

BRUCE LEHMAN

*Attesting Officer*  *Commissioner of Patents and Trademarks*